United States Patent
Enderlin-Paput et al.

(10) Patent No.: US 9,540,399 B2
(45) Date of Patent: Jan. 10, 2017

(54) QUINOLONE DERIVATIVES

(71) Applicant: ACTELION PHARMACEUTICALS LTD, Allschwil (CH)

(72) Inventors: Stephanie Enderlin-Paput, Allschwil (CH); Christian Hubschwerlen, Durmenach (FR); Georg Rueedi, Allschwil (CH); Cornelia Zumbrunn, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 14/888,581

(22) PCT Filed: Apr. 30, 2014

(86) PCT No.: PCT/IB2014/061099
§ 371 (c)(1),
(2) Date: Nov. 2, 2015

(87) PCT Pub. No.: WO2014/178008
PCT Pub. Date: Nov. 6, 2014

(65) Prior Publication Data
US 2016/0060276 A1    Mar. 3, 2016

(30) Foreign Application Priority Data
May 2, 2013   (WO) ................. PCT/IB2013/053472

(51) Int. Cl.
*C07D 519/00*   (2006.01)
*C07D 498/04*   (2006.01)
*C07D 513/04*   (2006.01)

(52) U.S. Cl.
CPC ........... *C07D 519/00* (2013.01); *C07D 498/04* (2013.01); *C07D 513/04* (2013.01)

(58) Field of Classification Search
CPC .... C07D 519/00; C07D 513/04; C07D 498/04
USPC ................... 514/224.2, 230.5; 544/48, 105
See application file for complete search history.

(56) References Cited

U.S. PATENT DOCUMENTS

| 6,777,420 | B2 | 8/2004 | Zhi et al. |
| 8,222,407 | B2 | 7/2012 | Fukuda et al. |

FOREIGN PATENT DOCUMENTS

| EP | 0 027 752 B1 | 12/1883 |
| EP | 0 187 376 B1 | 5/1992 |
| EP | 2 017 261 A1 | 1/2009 |
| WO | WO 96/04286 A1 | 2/1996 |
| WO | WO 02/056882 A1 | 7/2002 |
| WO | WO 02/102792 A1 | 12/2002 |
| WO | WO 2004/087145 A2 | 10/2004 |
| WO | WO 2006/081289 A2 | 8/2006 |
| WO | WO 2008/006648 A1 | 1/2008 |
| WO | WO 2009/064792 A1 | 5/2009 |
| WO | WO 2010/019208 A1 | 2/2010 |
| WO | WO 2010/025906 A2 | 3/2010 |
| WO | WO 2010/045987 A1 | 4/2010 |
| WO | WO 2010/084152 A1 | 7/2010 |
| WO | WO 2011/034971 A1 | 3/2011 |
| WO | WO 2011/037433 A2 | 3/2011 |
| WO | WO 2011/094260 A2 | 8/2011 |
| WO | WO 2012/101013 A1 | 8/2012 |
| WO | WO 2013/029548 A1 | 3/2013 |
| WO | WO 2013/068948 A1 | 5/2013 |
| WO | WO 2013/142628 A2 | 9/2013 |

OTHER PUBLICATIONS

International Search Report of PCT/IB2014/061099 dated Aug. 7, 2014.
"Methods for Dilution Antimicrobial Susceptibility Tests for Bacteria that Grow Aerobically", Approved standard, 7th ed., (CLSI) Document M7-A7, USA, 2006.
Bellina et al., "Palladium Catalysts for the Suzuki Cross-Coupling Reaction: An Overview of Recent Advances", Synthesis (2004), 2419-2440.
Chang et al., "Triazolinones as Nonpeptide Angiotension II Antagonists. 1. Synthesis and Evaluation of Potent 2,4,5-Trisubstituted Triazolinones", J. Med. Chem. (1993), 36, 2558-2568.
Fu, "The Development of Versatile Methods for Palladium-Catalyzed Coupling Reactions of Aryl Electrophiles through the Use of P(t-BU)3 and PCy3 as Ligands", Acc. Chem. Res. (2008), 41, 1555-1564.
Greene et al., Protecting Groups in Organic Synthesis, 3rd Ed. (1999), 369-441.
Greene et al., Protecting Groups in Organic Synthesis, 3rd Ed. (1999), 494-653.
Greene et al., Protecting Groups in Organic Synthesis, Wiley-Interscience, 1999.
Kantchev et al., "Pd-N-Heterocyclic Carbene (NHC) Catalysts for Cross-Coupling Reactions", Aldrichimica Acta (2006), 39. 97-111.

(Continued)

*Primary Examiner* — Kahsay Habte
(74) *Attorney, Agent, or Firm* — Arent Fox LLP

(57) ABSTRACT

The invention relates to antibacterial compounds of formula I

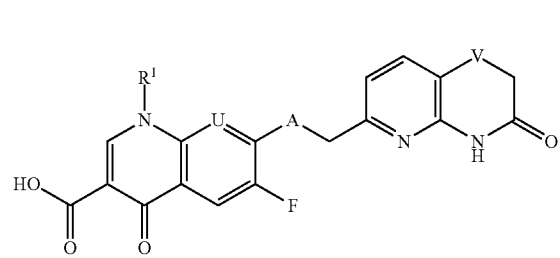

wherein $R^1$, U, V and A are as defined in the description, to pharmaceutical compositions containing them and uses of these compounds in the manufacture of medicaments for the treatment of bacterial infections.

16 Claims, No Drawings

(56) References Cited

OTHER PUBLICATIONS

Karoli et al., "Structure aided design of chimeric antibiotics," Bioorganic & Medicinal Chemistry Letters 22(2012) 2428-2433.
Larock, Comprehensive Organic Transformations. A guide to Functional Group Preparations, 2nd Edition (1999): Section Amines, 779.
Mauger et al., "Synthetic Applications of Buchwald's Phosphines in Palladium-Catalyzed Aromatic-Bond-Forming Reactions", Aldrichimica Acta (2006), 39, 17-24.
Miyaura et al., "Palladium-Catalyzed Cross-Coupling Reactions of Organoboron Compounds", Chem. Rev. 1995, 2457-2483.
Parrill et al., "Virtual screening approaches for the identification of non-lipid autotaxin inhibitors," Bioorganic & Medicinal Chemistry 16 (2008) 1784-1795.
Remington, "Pharmaceutical Manufacturing", The Science and Practice of Pharmacy, 21st Edition, Part 5 (2005).
Sanford et al., "The Sanford Guide to Antimicrobial Therapy", 26th Edition, (Antimicrobial Therapy, Inc. 1996).
Sato et al., "One-pot reductive amination of aldehydes and ketones with alpha-picoline-borane in.methanol, in water, and in neat conditions", Tetrahedon (2004), 60, 7899-7906.
Stahl et al., Handbook of Pharmaceutical Salts Properties, Selection, and Use (2008).
Wainwright et al., "Phenothiazinium-fluoroquinolone drug conjugates", International Journal of Antimicrobial Agents 35 (2010) 405-409.
Wang et al., "Synthesis, antimycobacterial and antibacterial activity of ciprofloxacin derivatives containing a N-substituted benzyl moiety," Bioorganic & Medicinal Chemistry Letters 22 (2012) 5971-5975.
Wouters et al., Pharmaceutical Salts and Co-crystals (2012).

QUINOLONE DERIVATIVES

CROSS-REFERENCE TO RELATED APPLICATIONS

This application is a National Stage entry of International Application No. PCT/IB2014/061099, filed Apr. 30, 2014, which claims priority to International Application No. PCT/IB2013/053472, filed May 2, 2013. The disclosures of the prior applications are hereby incorporated in their entirety by reference.

The present invention concerns antibacterial quinolone derivatives, pharmaceutical compositions containing them and uses of these compounds in the manufacture of medicaments for the treatment of bacterial infections. These compounds are useful antimicrobial agents effective against a variety of human and veterinary pathogens including among others Gram-positive and Gram-negative aerobic and anaerobic bacteria and mycobacteria, and especially multi-drug-resistant Gram negative bacteria.

The intensive use of antibiotics has exerted a selective evolutionary pressure on microorganisms to produce genetically based resistance mechanisms. Modern medicine and socio-economic behaviour exacerbate the problem of resistance development by creating slow growth situations for pathogenic microbes, e.g. in artificial joints, and by supporting long-term host reservoirs, e.g. in immuno-compromised patients.

In hospital settings, an increasing number of strains of *Staphylococcus aureus*, *Streptococcus pneumoniae*, *Enterococcus* spp., Enterobacteriacea, *Acinetobacter baumanii* and *Pseudomonas aeruginosa*, major sources of infections, are becoming multi-drug resistant and therefore difficult if not impossible to treat. This is particularly the case for Gram negative organisms where the situation is getting worrisome since no novel agents have been approved for decades and the development pipeline looks empty.

Therefore, there is a huge medical need for new antibacterial compounds addressing Gram negative resistant bacteria, in particular third generation cephalosporins- and carbapenem-resistant *Klebsiella pneumonia* and multi-drug-resistant *Pseudomonas aeruginosa* and *Acinetobacter baumanii*.

WO2004/087145, WO2006/081289, WO2008/006648, WO 2010/045987 and WO2010/084152 describe antibacterial compounds comprising the bicyclic pyridine fragment

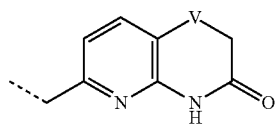

linked through a spacer to quinolines, quinolin-2-ones and their azaisosteres.

Several publications relate to compounds harboring a 7-fluoroquinolone or a 7-fluoronaphthyridinone fragment (see for example: International Journal of Antimicrobial Agents 2010, 35(4), 405-409; Bioorganic & Medicinal Chemistry 2008, 16(4), 1784-1795; Bioorganic & Medicinal Chemistry Letters 2012, 22(7), 2428-2433; Bioorganic & Medicinal Chemistry Letters 2012, 22(18), 5971-5975; WO 2011/094260; WO 2011/034971; WO 2010/025906; WO 2010/019208; WO 2009/064792; U.S. Pat. No. 8,222,407; U.S. Pat. No. 6,777,420; WO 2002/102792; WO 1996/004286; WO2013/029548; WO2013/142628).

WO2013/068948 discloses antibacterial compounds comprising an oxazolidine moiety.

The instant invention provides novel antibacterial compounds combining a quinolone or naphthyridone motif and said bicyclic pyridine fragment.

1) A first embodiment of the present invention relates to compounds of formula I

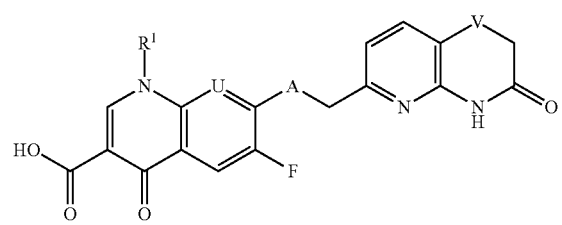

wherein $R^1$ represents $(C_1-C_3)$alkyl (especially methyl or ethyl), or $R^1$ represents $(C_3-C_5)$cycloalkyl (especially cyclopropyl) (wherein in a first sub-embodiment $R^1$ represents methyl or ethyl, especially methyl; and in a second sub-embodiment $R^1$ represents cyclopropyl);

U represents CH or N;

V represents O or S (especially S); and

A represents a linker group consisting of a 1-, 2-, or 3-membered saturated straight chain group which is attached to, or interrupted by a 6-membered cyclic group selected from cyclohexan-1,4-diyl, piperidin-1,4-diyl, and piperazin-1,4-diyl; wherein said linker group (i.e. the group comprising both the straight chain group and the 6-membered cyclic group) contains a total of two or three nitrogen atoms, wherein said nitrogen atoms are separated from each other by at least two carbon atoms.

2) A second embodiment relates to compounds of formula I according to embodiment 1); wherein $R^1$ represents methyl or ethyl; or $R^1$ represents cyclopropyl (especially $R^1$ represents methyl or cyclopropyl)

(wherein in a first sub-embodiment 2a), $R^1$ represents methyl; and in a second sub-embodiment 2b), $R^1$ represents cyclopropyl);

U represents CH or N;

V represents O or S (especially S); and

A represents a group selected from the following groups:

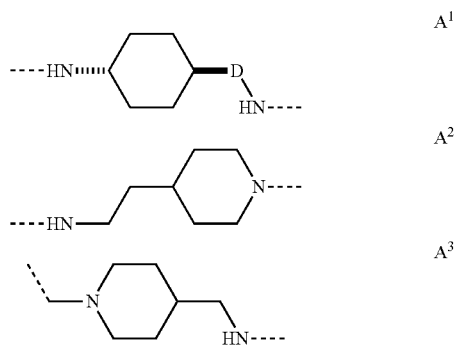

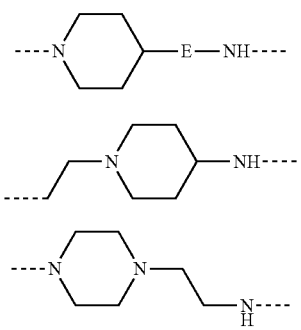

wherein
D represents a bond or CH$_2$; and
E represents a bond, CH$_2$ or CH$_2$CH$_2$;

(wherein, in a sub-embodiment, A is especially selected from the groups A$^1$ and/or A$^4$).

In this patent application, bonds drawn as dotted lines show the points of attachment of the radical drawn. In case of two points of attachment, molecules or radicals are to be read from left to right. For example, the radical A$^2$ drawn below

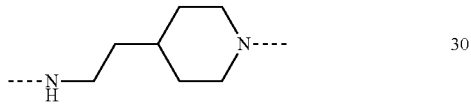

means a bivalent 4-(2-amino-ethyl)-piperidin-1-yl group wherein the left terminal nitrogen atom bearing one hydrogen atom is attached to the naphthyridinone/quinolone ring of the compounds of formula I, whereas the nitrogen atom of the piperidine ring is attached to the CH$_2$ group making the connection to the 3-oxo-3,4-dihydro-2H-pyrido[3,2-b][1,4]oxazine-6-yl/the 3-oxo-3,4-dihydro-2H-pyrido[3,2-b][1,4]thiazine-6-yl moiety of the compounds of formula I.

For avoidance of any doubt, cyclohexan-1,4-diyl moieties when used for the group A$^1$:

are defined as having a fixed relative configuration which is trans [or (1r,4r)].

Various embodiments of the invention are presented hereafter:

3) A further embodiment relates to compounds of formula I according to embodiments 1) or 2), wherein V represents S.

4) A further embodiment relates to compounds of formula I according to embodiments 1) or 2), wherein V represents O.

5) A further embodiment relates to compounds of formula I according to any one of embodiments 1) to 4), wherein U represents N.

6) A further embodiment relates to compounds of formula I according to any one of embodiments 1) to 4), wherein U represents CH.

7) A further embodiment relates to compounds of formula I according to any one of embodiments 1) to 6), wherein A represents a group selected from the following groups:

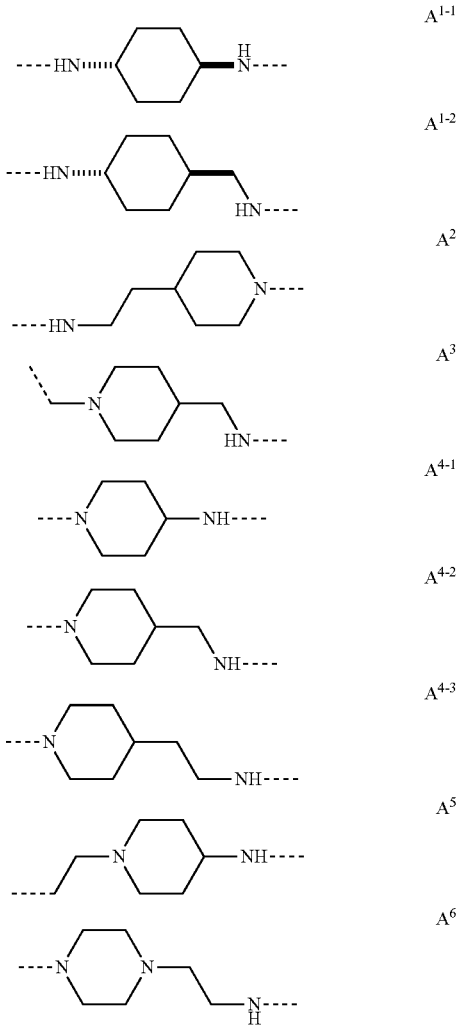

(wherein, in a sub-embodiment, A is notably selected from the groups A$^1$ and/or A$^4$; especially A is A$^{1-2}$ or A$^{4-3}$).

8) A further embodiment relates to compounds of formula I according to any one of embodiments 1) to 6), wherein A represents a group selected from the following groups:

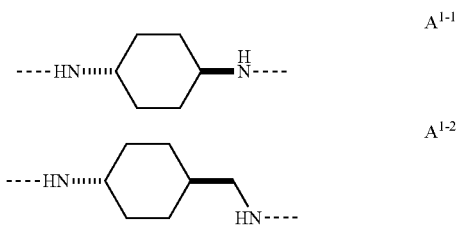

(especially A represents a group A$^{1-2}$).

9) A further embodiment relates to compounds of formula I according to any one of embodiments 1) to 6), wherein A represents a group selected from the following groups:

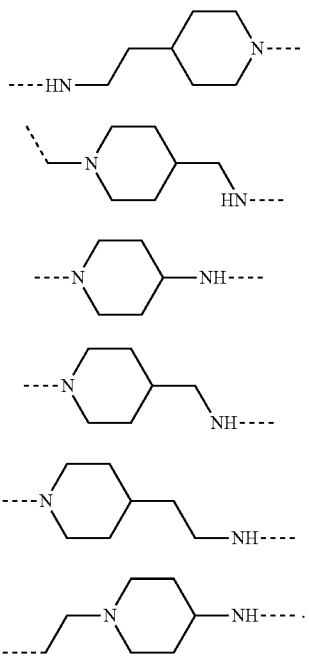 A²

A³

A⁴⁻¹

A⁴⁻²

A⁴⁻³

A⁵

10) A further embodiment relates to compounds of formula I according to any one of embodiments 1) to 6), wherein A represents a group selected from the following groups:

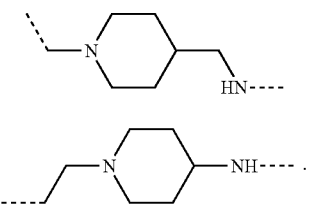 A³

A⁵

11) A further embodiment relates to compounds of formula I according to any one of embodiments 1) to 6), wherein A represents:

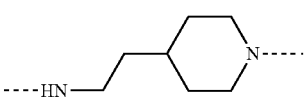 A²

12) A further embodiment relates to compounds of formula I according to any one of embodiments 1) to 6), wherein A represents a group selected from the following groups:

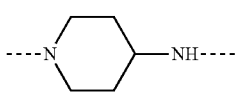 A⁴⁻¹

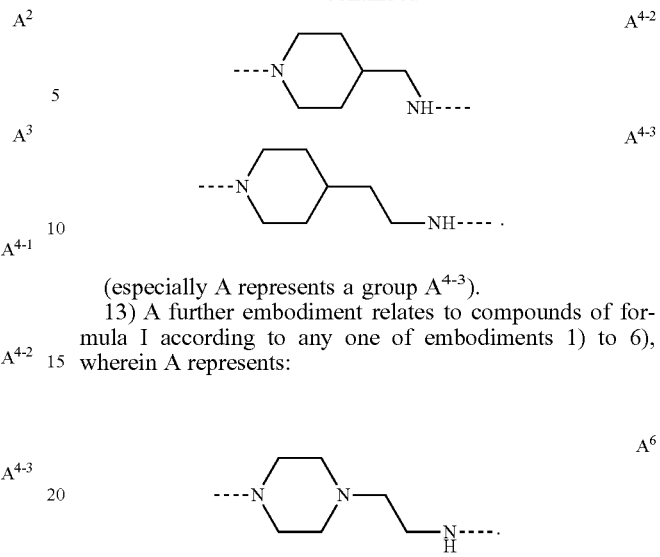 A⁴⁻²

A⁴⁻³

(especially A represents a group A⁴⁻³).

13) A further embodiment relates to compounds of formula I according to any one of embodiments 1) to 6), wherein A represents:

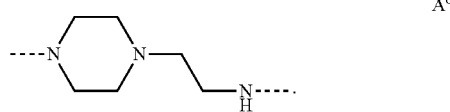 A⁶

14) Particular compounds of formula I according to embodiment 1) are selected from the group consisting of:
trans-1-Cyclopropyl-6-fluoro-4-oxo-7-(4-{[(3-oxo-3,4-dihydro-2H-pyrido[3,2-b][1,4]thiazin-6-ylmethyl)-amino]-methyl}-cyclohexylamino)-1,4-dihydro-[1,8]naphthyridine-3-carboxylic acid;
trans-1-Cyclopropyl-6-fluoro-4-oxo-7-{4-[(3-oxo-3,4-dihydro-2H-pyrido[3,2-b][1,4]thiazin-6-ylmethyl)-amino]-cyclohexylamino}-1,4-dihydro-[1,8]naphthyridine-3-carboxylic acid; 1-Cyclopropyl-6-fluoro-4-oxo-7-(2-{4-[(3-oxo-3,4-dihydro-2H-pyrido[3,2-b][1,4]thiazin-6-ylmethyl)-amino]-piperidin-1-yl}-ethyl)-1,4-dihydro-[1,8]naphthyridine-3-carboxylic acid;
1-Cyclopropyl-6-fluoro-4-oxo-7-(4-{2-[(3-oxo-3,4-dihydro-2H-pyrido[3,2-b][1,4]thiazin-6-ylmethyl)-amino]-ethyl}-piperazin-1-yl)-1,4-dihydro-[1,8]naphthyridine-3-carboxylic acid;
1-Cyclopropyl-6-fluoro-4-oxo-7-(4-{2-[(3-oxo-3,4-dihydro-2H-pyrido[3,2-b][1,4]thiazin-6-ylmethyl)-amino]-ethyl}-piperidin-1-yl)-1,4-dihydro-[1,8]naphthyridine-3-carboxylic acid;
1-Cyclopropyl-6-fluoro-4-oxo-7-{2-[(3-oxo-3,4-dihydro-2H-pyrido[3,2-b][1,4]thiazin-6-ylmethyl)-piperidin-4-yl]-ethylamino}-1,4-dihydro-[1,8]naphthyridine-3-carboxylic acid;
1-Cyclopropyl-6-fluoro-4-oxo-7-(4-{[(3-oxo-3,4-dihydro-2H-pyrido[3,2-b][1,4]thiazin-6-ylmethyl)-amino]-methyl}-piperidin-1-yl)-1,4-dihydro-[1,8]naphthyridine-3-carboxylic acid;
trans-1-Cyclopropyl-6-fluoro-4-oxo-7-(4-{[(3-oxo-3,4-dihydro-2H-pyrido[3,2-b][1,4]oxazin-6-ylmethyl)-amino]-methyl}-cyclohexylamino)-1,4-dihydro-[1,8]naphthyridine-3-carboxylic acid;
1-Cyclopropyl-6-fluoro-4-oxo-7-(4-{[(3-oxo-3,4-dihydro-2H-pyrido[3,2-b][1,4]thiazin-6-ylmethyl)-amino]-methyl}-piperidin-1-ylmethyl)-1,4-dihydro-[1,8]naphthyridine-3-carboxylic acid;
1-Cyclopropyl-6-fluoro-4-oxo-7-{4-[(3-oxo-3,4-dihydro-2H-pyrido[3,2-b][1,4]thiazin-6-ylmethyl)-amino]-piperidin-1-yl}-1,4-dihydro-[1,8]naphthyridine-3-carboxylic acid; and
1-Cyclopropyl-6-fluoro-4-oxo-7-(4-{2-[(3-oxo-3,4-dihydro-2H-pyrido[3,2-b][1,4]thiazin-6-ylmethyl)-amino]-ethyl}-piperazin-1-yl)-1,4-dihydro-quinoline-3-carboxylic acid.

15) Further particular compounds of formula I according to embodiment 1) are selected from the group consisting of:

1-Cyclopropyl-6-fluoro-4-oxo-7-(4-{2-[(3-oxo-3,4-dihydro-2H-pyrido[3,2-b][1,4]oxazin-6-ylmethyl)-amino]-ethyl}-piperazin-1-yl)-1,4-dihydro-[1,8]naphthyridine-3-carboxylic acid;

trans-6-Fluoro-1-methyl-4-oxo-7-(4-{[(3-oxo-3,4-dihydro-2H-pyrido[3,2-b][1,4]thiazin-6-ylmethyl)-amino]-methyl}-cyclohexylamino)-1,4-dihydro-[1,8]naphthyridine-3-carboxylic acid;

trans-6-Fluoro-1-methyl-4-oxo-7-(4-{[(3-oxo-3,4-dihydro-2H-pyrido[3,2-b][1,4]oxazin-6-ylmethyl)-amino]-methyl}-cyclohexylamino)-1,4-dihydro-[1,8]naphthyridine-3-carboxylic acid;

trans-1-Ethyl-6-fluoro-4-oxo-7-(4-{[(3-oxo-3,4-dihydro-2H-pyrido[3,2-b][1,4]thiazin-6-ylmethyl)-amino]-methyl}-cyclohexylamino)-1,4-dihydro-[1,8]naphthyridine-3-carboxylic acid;

6-Fluoro-1-methyl-4-oxo-7-(4-{2-[(3-oxo-3,4-dihydro-2H-pyrido[3,2-b][1,4]oxazin-6-ylmethyl)-amino]-ethyl}-piperidin-1-yl)-1,4-dihydro-[1,8]naphthyridine-3-carboxylic acid; and 6-Fluoro-1-methyl-4-oxo-7-(4-{2-[(3-oxo-3,4-dihydro-2H-pyrido[3,2-b][1,4]thiazin-6-ylmethyl)-amino]-ethyl}-piperidin-1-yl)-1,4-dihydro-[1,8]naphthyridine-3-carboxylic acid.

16) The invention, thus, relates to compounds of the formula I as defined in embodiment 1), or to such compounds further limited by the characteristics of any one of embodiments 2) to 15), under consideration of their respective dependencies; to pharmaceutically acceptable salts thereof; and to the use of such compounds as medicaments especially for the prevention or treatment of a bacterial infection as set out in the description, in particular for the prevention or treatment of bacterial infections such as urinary tract infections; systemic infections (bacteraemia and sepsis); surgical infections; intraabdominal infections and lung infections (including those in patients with cystic fibrosis) caused by Gram negative bacteria such as especially *Acinetobacter baumannii*, *Burkholderia* (e.g., *Burkholderia cepacia*), *Citrobacter* spp., *Enterobacter aerogenes*, *Enterobacter cloacae*, *Escherichia coli*, *Klebsiella oxytoca*, *Klebsiella pneumoniae*, *Serratia marcescens*, *Stenotrophomonas maltophilia*, and *Pseudomonas aeruginosa*. Especially the following embodiments relating to the compounds of formula I are thus possible and intended and herewith specifically disclosed in individualized form:

1, 2, 3+1, 3+2, 4+1, 4+2, 5+1, 5+2, 5+3+1, 5+3+2, 5+4+1, 5+4+2, 6+1, 6+2, 6+3+1, 6+3+2, 6+4+1, 6+4+2, 7+1, 7+2, 7+3+1, 7+3+2, 7+4+1, 7+4+2, 7+5+1, 7+5+2, 7+5+3+1, 7+5+3+2, 7+5+4+1, 7+5+4+2, 7+6+1, 7+6+2, 7+6+3+1, 7+6+3+2, 7+6+4+1, 7+6+4+2, 8+1, 8+2, 8+3+1, 8+3+2, 8+4+1, 8+4+2, 8+5+1, 8+5+2, 8+5+3+1, 8+5+3+2, 8+5+4+1, 8+5+4+2, 8+6+1, 8+6+2, 8+6+3+1, 8+6+3+2, 8+6+4+1, 8+6+4+2, 9+1, 9+2, 9+3+1, 9+3+2, 9+4+1, 9+4+2, 9+5+1, 9+5+2, 9+5+3+1, 9+5+3+2, 9+5+4+1, 9+5+4+2, 9+6+1, 9+6+2, 9+6+3+1, 9+6+3+2, 9+6+4+1, 9+6+4+2, 10+1, 10+2, 10+3+1, 10+3+2, 10+4+1, 10+4+2, 10+5+1, 10+5+2, 10+5+3+1, 10+5+3+2, 10+5+4+1, 10+5+4+2, 10+6+1, 10+6+2, 10+6+3+1, 10+6+3+2, 10+6+4+1, 10+6+4+2, 11+1, 11+2, 11+3+1, 11+3+2, 11+4+1, 11+4+2, 11+5+1, 11+5+2, 11+5+3+1, 11+5+3+2, 11+5+4+1, 11+5+4+2, 11+6+1, 11+6+2, 11+6+3+1, 11+6+3+2, 11+6+4+1, 11+6+4+2, 12+1, 12+2, 12+3+1, 12+3+2, 12+4+1, 12+4+2, 12+5+1, 12+5+2, 12+5+3+1, 12+5+3+2, 12+5+4+1, 12+5+4+2, 12+6+1, 12+6+2, 12+6+3+1, 12+6+3+2, 12+6+4+1, 12+6+4+2, 13+1, 13+2, 13+3+1, 13+3+2, 13+4+1, 13+4+2, 13+5+1, 13+5+2, 13+5+3+1, 13+5+3+2, 13+5+4+1, 13+5+4+2, 13+6+1, 13+6+2, 13+6+3+1, 13+6+3+2, 13+6+4+1, 13+6+4+2.

In the list above, the numbers refer to the embodiments according to their numbering provided hereinabove whereas "+" indicates the dependency from another embodiment. The different individualized embodiments are separated by commas. In other words, "8+3+1" for example refers to embodiment 8) depending on embodiment 3), depending on embodiment 1), i.e. embodiment "8+3+1" corresponds to the compounds of embodiment 1) further limited by the features of the embodiments 3) and 8).

Definitions provided herein are intended to apply uniformly to the compounds of formula I as defined in any one of embodiments 1) to 16), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The term "alkyl", used alone or in combination, refers to a saturated straight or branched chain hydrocarbon group containing from one to four carbon atoms. The term "$(C_1-C_x)$alkyl" (x being an integer) refers to an alkyl group containing 1 to x carbon atoms. For example, a $(C_1-C_4)$alkyl group contains from one to four carbon atoms. Representative examples of alkyl groups include methyl, ethyl, propyl, iso-propyl, n-butyl, iso-butyl, sec-butyl and tert-butyl. Preferred are methyl and ethyl. Most preferred is methyl. For the substituent R', the term $(C_1-C_3)$alkyl notably means methyl or ethyl; preferred is methyl.

The term "cycloalkyl", used alone or in combination, refers to a saturated cyclic hydrocarbon group containing from three to seven carbon atoms. The term "$(C_3-C_x)$cycloalkyl" (x being an integer) refers to a cycloalkyl group containing 3 to x carbon atoms. For example, a $(C_3-C_5)$cycloalkyl group contains from three to five carbon atoms. Representative examples of cycloalkyl groups include cyclopropyl, cyclobutyl, and cyclopentyl. For the substituent R', the term $(C_3-C_5)$cycloalkyl preferably means cyclopropyl.

The term "quinolone-resistant", or "methicillin-resistant" associated to a bacterial strain, when used in this text, refer to a bacterial strain against which respectively ciprofloxacin, or methicillin have a Minimal Inhibitory Concentration of at least 16 mg/l (said Minimal Inhibitory Concentration being measured with the standard method described in "Methods for Dilution Antimicrobial Susceptibility Tests for Bacteria that Grow Aerobically", Approved standard, 7$^{th}$ ed., Clinical and Laboratory Standards Institute (CLSI) Document M7-A7, Wayne, Pa., USA, 2006). The term "multi-drug-resistant" associated to a bacterial strain when used in this text, refers to a bacterial strain that is resistant to more than three classes of antibiotics.

Any reference to a compound of formula I is to be understood as referring also to the salts, especially the pharmaceutically acceptable salts of such a compound, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quere (Eds.), RSC Publishing, 2012.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C. The term "room temperature" as used herein refers to a temperature of about 25° C.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

The present invention also includes isotope labeled, especially $^2$H (deuterium) labeled compounds of formula I as defined in any one of embodiments 1) to 16) which compounds are identical to the compounds of formula I except that one or more atoms have each been replaced by an atom having the same atomic number but an atomic mass different from the atomic mass usually found in nature. Isotope labeled, especially 2H (deuterium) labeled compounds of formula I and salts thereof are within the scope of the present invention. Substitution of hydrogen with the heavier isotope 2H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula I are not isotope labeled, or they are labeled only with one or more deuterium atoms. In a sub-embodiment, the compounds of formula I are not isotope labeled at all. Isotope labeled compounds of formula I may be prepared in analogy to the methods described hereinafter, but using the appropriate isotope variation of suitable reagents or starting materials.

The compounds formula I as defined in any one of embodiments 1) to 16) and their pharmaceutically acceptable salts can be used as medicaments, e.g. in the form of pharmaceutical compositions for enteral (such especially oral) or parenteral administration (including topical application or inhalation).

In a preferred embodiment of the invention, the administered amount of compound of formula I as defined in any one of embodiments 1) to 16) will be comprised between 1 mg and 2000 mg per day, particularly between 50 mg and 1500 mg per day, more particularly between 100 mg and 1000 mg per day, especially between 250 mg and 1000 mg per day.

A further aspect of the invention are pharmaceutical compositions comprising a compound of formula I as defined in any one of embodiments 1) to 16), or a pharmaceutically acceptable salt thereof, and a pharmaceutically acceptable excipient/carrier material. A pharmaceutical composition according to the present invention contains at least one compound of formula I (or a pharmaceutically acceptable salt thereof) as the active agent, and may also contain additional known antibiotics.

The production of the pharmaceutical compositions can be effected in a manner which will be familiar to any person skilled in the art (see for example Remington, The Science and Practice of Pharmacy, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The compounds of formula I according to the invention, i.e. a compound of formula I as defined in any one of embodiments 1) to 16) above, are suitable for the use as chemotherapeutic active compounds in human and veterinary medicine and as substances for preserving inorganic and organic materials in particular all types of organic materials for example polymers, lubricants, paints, fibres, leather, paper and wood.

The compounds of formula I as defined in any one of embodiments 1) to 16) exhibit antibacterial activity especially against Gram-negative organisms. They may be used to treat bacterial infections in mammals, especially humans. The compounds may also be used for veterinary applications, such as treating infections in livestock and companion animals, including pigs, ruminants, horses, dogs, cats and poultry.

The compounds of formula I as defined in any one of embodiments 1) to 16) are in particular useful for treating a variety of bacterial infections, especially infections mediated by Gram-negative bacteria. Such bacterial infections include nosocomial pneumonia, urinary tract infections, systemic infections (bacteraemia and sepsis), skin and soft tissue infections, surgical infections, intraabdominal infections, lung infections (including those in patients with cystic fibrosis), endocarditis, diabetic foot infections, osteomyelitis, and central nervous system infections. In a sub-embodiment, particular infections caused by Gram-negative bacteria are selected from urinary tract infections; systemic infections (bacteraemia and sepsis); surgical infections; intraabdominal infections and lung infections (including those in patients with cystic fibrosis); notably selected from urinary tract infections; intraabdominal infections and lung infections (including those in patients with cystic fibrosis); especially from urinary tract infections and intraabdominal infections.

The compounds of formula I as defined in any one of embodiments 1) to 16) may be used for the treatment or prevention of bacterial infections mediated by fermentative or non-fermentative Gram negative bacteria (especially the above listed bacterial infections mediated by Gram-negative bacteria), in particular those caused by susceptible and multi-drug resistant (MDR) Gram-negative bacteria. Examples of such Gram-negative bacteria include *Acinetobacter* spp. such as *Acinetobacter baumannii* or *Acinetobacter haemolyticus, Actinobacillus actinomycetemcomitans, Achromobacter* spp. such as *Achromobacter xylosoxidans* or *Achromobacter faecalis, Aeromonas* spp. such as *Aeromonas hydrophila, Bacteroides* spp. such as *Bacteroides fragilis, Bacteroides theataioatamicron, Bacteroides distasonis, Bacteroides ovatus* or *Bacteroides vulgatus, Bartonella hensenae, Bordetella* spp. such as *Bordetella pertussis, Borrelia* spp. such as *Borrelia Burgdorferi, Brucella* spp. such as *Brucella melitensis, Burkholderia* spp.

such as *Burkholderia cepacia*, *Burkholderia pseudomallei* or *Burkholderia mallei*, *Campylobacter* spp. such as *Campylobacter jejuni*, *Campylobacter fetus* or *Campylobacter coli*, *Cedecea*, *Chlamydia* spp. such as *Chlamydia pneumoniae*, *Chlamydia trachomatis*, *Citrobacter* spp. such as *Citrobacter diversus* (*koseri*) or *Citrobacter freundii*, *Coxiella burnetii*, *Edwardsiella* spp. such as *Edwarsiella tarda*, *Ehrlichia chafeensis*, *Eikenella corrodens*, *Enterobacter* spp. such as *Enterobacter cloacae*, *Enterobacter aerogenes*, *Enterobacter agglomerans*, *Escherichia coli*, *Francisella tularensis*, *Fusobacterium* spp., *Haemophilus* spp. such as *Haemophilus influenzae* (beta-lactamase positive and negative) or *Haemophilus ducreyi*, *Helicobacter pylori*, *Kingella kingae*, *Klebsiella* spp. such as *Klebsiella oxytoca*, *Klebsiella pneumoniae* (including those encoding extended-spectrum beta-lactamases (hereinafter "ESBLs"), KPCs, CTX-M, metallo-beta-lactamases, and AmpC-type beta-lactamases that confer resistance to currently available cephalosporins, cephamycins, carbapenems, beta-lactams, and beta-lactams/beta-lactamase inhibitor combinations), *Klebsiella rhinoscleromatis* or *Klebsiella ozaenae*, *Legionella pneumophila*, *Mannheimia haemolyticus*, *Moraxella catarrhalis* (beta-lactamase positive and negative), *Morganella morganii*, *Neisseria* spp. such as *Neisseria gonorrhoeae* or *Neisseria meningitidis*, *Pasteurella* spp. such as *Pasteurella multocida*, *Plesiomonas shigelloides*, *Porphyromonas* spp. such as *Porphyromonas asaccharolytica*, *Prevotella* spp. such as *Prevotella corporis*, *Prevotella intermedia* or *Prevotella endodontalis*, *Proteus* spp. such as *Proteus mirabilis*, *Proteus vulgaris*, *Proteus penneri* or *Proteus myxofaciens*, *Porphyromonas asaccharolytica*, *Plesiomonas shigelloides*, *Providencia* spp. such as *Providencia stuartii*, *Providencia rettgeri* or *Providencia alcalifaciens*, *Pseudomonas* spp. such as *Pseudomonas aeruginosa* or *Pseudomonas fluorescens*, *Ricketsia prowazekii*, *Salmonella* spp. such as *Salmonella typhi* or *Salmonella paratyphi*, *Serratia marcescens*, *Shigella* spp. such as *Shigella flexneri*, *Shigella boydii*, *Shigella sonnei* or *Shigella dysenteriae*, *Streptobacillus moniliformis*, *Stenotrophomonas maltophilia*, *Treponema* spp., *Vibrio* spp. such as *Vibrio cholerae*, *Vibrio parahaemolyticus*, *Vibrio vulnificus*, *Vibrio alginolyticus*, *Yersinia* spp. such as *Yersinia enterocolitica*, *Yersinia pestis*, *Yersinia pseudotuberculosis*.

In a preferred embodiment, examples of such Gram-negative bacteria are selected from *Acinetobacter baumannii*, *Burkholderia* (e.g., *Burkholderia cepacia*), *Citrobacter* spp., *Enterobacter aerogenes*, *Enterobacter cloacae*, *Escherichia coli*, *Klebsiella oxytoca*, *Klebsiella pneumoniae*, *Serratia marcescens*, *Stenotrophomonas maltophilia*, and *Pseudomonas aeruginosa*. In sub-embodiment, such Gram-negative bacteria are especially selected from *Citrobacter* spp., *Enterobacter aerogenes*, *Enterobacter cloacae*, *Escherichia coli*, *Klebsiella oxytoca*, *Klebsiella pneumoniae*, *Serratia marcescens*, *Stenotrophomonas maltophilia*, and *Acinetobacter baumannii*. In a further sub-embodiment, particular Gram-negative bacteria are *Acinetobacter baumannii* and, especially, *Klebsiella pneumonia*.

The preceding lists of infections and pathogens are to be interpreted merely as examples and in no way as limiting.

Other bacterial infections and disorders related to infections that may be treated or prevented in accord with the method of the present invention are referred to in J. P. Sanford et al., "The Sanford Guide to Antimicrobial Therapy," 26th Edition, (Antimicrobial Therapy, Inc., 1996).

The compounds of formula I can be manufactured in accordance with the present invention using the procedures described hereafter.

Preparation of the Compounds of Formula I
Abbreviations:
The following abbreviations are used throughout the specification and the examples:
Ac acetyl
AcOH acetic acid
Alloc allyloxycarbonyl
aq. aqueous
Boc tert-butoxycarbonyl
BuLi n-butyl lithium
Cbz benzyloxycarbonyl
CC column chromatography over silica gel
Cipro ciprofloxacin
Cy cyclohexyl
DAD diode array detection
dba dibenzylideneacetone
DCE 1,2-dichloroethane
DCM dichloromethane
DIPEA N,N-diisopropylethylamine
DMAP 4-dimethylaminopyridine
DMF N,N-dimethylformamide
DMSO dimethylsulfoxide
EA ethyl acetate
ELSD evaporative light scattering detector
ESI electron spray ionisation
Et ethyl
EtOH ethanol
Hept heptane
Hex hexane
HexLi n-hexyl lithium
HPLC high pressure liquid chromatography
HV high vacuum conditions
LC liquid chromatography
Me methyl
MeCN acetonitrile
MeOH methanol
MS mass spectroscopy
NMO N-methylmorpholine N-oxide
NMP N-methyl 2-pyrrolidone
org. organic
PEPPSI™-IPr [1,3-bis(2,6-diisopropylphenyl)imidazol-2-ylidene](3-chloropyridyl)palladium(II) dichloride
Ph phenyl
Q-Phos 1,2,3,4,5-pentaphenyl-1'-(di-tert-butylphosphino)ferrocene
rt room temperature
sat. saturated
SK-CC01-A 2'-(dimethylamino)-2-biphenylyl-palladium(II) chloride dinorbornylphosphine complex
S-Phos 2-dicyclohexylphosphino-2',6'-dimethoxybiphenyl
tBu tert-butyl
TEA triethylamine
TFA trifluoroacetic acid
THF tetrahydrofuran
TLC thin layer chromatography
$t_R$ retention time
UV ultra-violet
General Reaction Techniques:
General Reaction Technique 1 (Hydrolysis of Esters into Carboxylic Acids):

When the ester side chain is a linear alkyl, the hydrolysis is usually performed by treatment with an alkali hydroxide such as LiOH, KOH or NaOH in a water-dioxane or water-THF mixture between 0° C. and 80° C. When the ester side chain is tert-butyl, the hydrolysis can also be performed in neat TFA or diluted TFA or HCl in an organic solvent such as ether or THF. When the ester side chain is the allyl group, the reaction is performed in presence of tetrakis(triphenylphosphine)palladium(0) in presence of an allyl cation scavenger such as morpholine, dimedone or tributyltin hydride between 0° C. and 50° C. in a solvent such as THF. When the ester side chain is benzyl, the reaction is performed under hydrogen in presence of a noble metal catalyst such as Pd/C in a solvent such as MeOH, THF or EA. Further strategies to introduce other acid protecting groups and general methods to remove them have been described in *Protecting Groups in Organic Synthesis* 3$^{rd}$ Ed; 1999, 369-441; T. W. Greene, P. G. M. Wuts; (Publisher: John Wiley and Sons, Inc., New York, N.Y.).

General Reaction Technique 2 (Reductive Amination):

The reaction between the amine and the aldehyde or ketone is performed in a solvent system allowing the removal of the formed water through physical or chemical means (e.g. distillation of the solvent-water azeotrope or presence of drying agents such as molecular sieves, MgSO$_4$ or Na$_2$SO$_4$). Such solvent is typically toluene, Hex, THF, DCM or DCE or a mixture of solvents such as DCE/MeOH. The reaction can be catalyzed by traces of acid (usually AcOH). The intermediate imine is reduced with a suitable reducing agent (e.g. NaBH$_4$, NaBH$_3$CN, or NaBH(OAc)$_3$ or through hydrogenation over a noble metal catalyst such as Pd/C. The reaction is carried out between −10° C. and 110° C., preferably between 0° C. and 60° C. The reaction can also be carried out in one pot. It can also be performed in protic solvents such as MeOH or water in presence of a picoline-borane complex (Sato et al., Tetrahedron (2004), 60, 7899-7906).

General Reaction Technique 3 (7-Chloro-Naphthyridin-4-One and 7-Chloro-Quinolone Substitution):

The amine derivative is reacted with 7-chloro-1-cyclopropyl-6-fluoro-1,4-dihydro-4-oxo-1,8-naphthyridine-3-carboxylic acid in presence of an organic base such as DIPEA or TEA in a solvent such as THF, DMF, MeCN or NMP between 0° C. and 120° C. for 3 to 24 h.

The amine derivative is reacted with 7-chloro-1-cyclopropyl-6-fluoro-4-oxoquinoline-3-carboxylic acid as above or alternatively the quinolone can be transiently activated as its alkyl, benzyl, allyl or boronate ester (e.g. the carboxylic acid is transformed into COOB(OAc)$_2$). In the particular case wherein a boronate ester is used, the reaction is followed by a treatment with an aq. inorganic acid such as HCl prior to purification; otherwise the ester is deprotected using general reaction technique 1. Further details can be found in *Comprehensive Organic Transformations. A guide to Functional Group Preparations;* 2$^{nd}$ Edition, R. C. Larock, Wiley-VC; New York, Chichester, Weinheim, Brisbane, Singapore, Toronto, 1999. Section Amines p. 779.

General Reaction Technique 4 (Suzuki Coupling):

The aromatic halide (typically a bromide) is reacted with the required boronic acid derivative or its boronate ester equivalent (e.g. pinacol ester) in the presence of a palladium catalyst and a base such as K$_2$CO$_3$, Cs$_2$CO$_3$, K$_3$PO$_4$, tBuONa or tBuOK between 20 and 120° C. in a solvent such as toluene, THF, dioxane, DME or DMF, usually in the presence of water (20 to 50%). Examples of typical palladium catalysts are triarylphosphine palladium complexes such as Pd(PPh$_3$)$_4$. These catalysts can also be prepared in situ from a common palladium source such as Pd(OAc)$_2$ or Pd$_2$(dba)$_3$ and a ligand such as trialkylphosphines (e.g. PCy$_3$ or P(tBu)$_3$), dialkylphosphinobiphenyls (e.g. S-Phos) or ferrocenylphosphines (e.g. Q-Phos). Alternatively, one can use a commercially available precatalyst based on palladacycle (e.g. SK-CC01-A) or N-heterocyclic carbene complexes (e.g. PEPPSI™-IPr). The reaction can also be performed by using the corresponding aromatic triflate. Further variations of the reaction are described in *Chem. Rev.* (1995), 95, 2457-2483, *Synthesis* (2004), 2419-2440, *Aldrichimica acta* (2006), 39, 17-24 and 97-111, *Acc. Chem. Res.* (2008), 41, 1555-1564, and references cited therein.

General Reaction Technique 5 (Amine Deprotection):

The Cbz protecting group is removed by hydrogenolysis over a noble metal catalyst (e.g. Pd/C or Pd(OH)$_2$/C). The Boc group is removed under acidic conditions such as HCl in an org. solvent such as MeOH or dioxane, or TFA neat or diluted in a solvent such DCM. The Alloc group is removed in presence of tetrakis(triphenylphosphine)palladium(0) in presence of an allyl cation scavenger such as morpholine, dimedone or tributyltin hydride between 0° C. and 50° C. in a solvent such as THF. Further general methods to remove amine protecting groups have been described in *Protecting Groups in Organic Synthesis,* 3rd Ed (1999), 494-653; T. W. Greene, P. G. M. Wuts; (Publisher: John Wiley and Sons, Inc., New York, N.Y.).

General Reaction Technique 6 (Azide into Amine):

The azides are hydrogenated over a noble metal catalyst such as Pd/C in solvent such as MeOH or EA. Alternatively; the reduction can be performed using PPh$_3$ in presence of water as described in *J. Med. Chem.* (1993), 36, 2558-68.

General Preparation Methods:

Preparation of the Compounds of Formula I:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

Sections hereafter describe general methods for preparing compounds of formula I. If not indicated otherwise, the generic groups R', U, V and A (including for example A$^1$, A$^2$, A$^3$, A$^4$, A$^5$, A$^6$, D and E) are as defined for formula I. Groups -G-NH— corresponding to the groups A$^1$, A$^3$, A$^4$, A$^5$ and/or A$^6$ mean that the group G represents the group A$^1$, A$^3$, A$^4$, A$^5$ and/or A$^6$ as defined but lacking the right terminal —NH— group. Likewise, groups —NH—Y— corresponding to the groups of formula A$^1$ and/or A$^2$ mean that the group Y represents the group A$^1$ or A$^2$ as defined but lacking the left terminal —NH— group.

General synthetic methods used repeatedly throughout the text below are referenced to and are described in the above section entitled "General reaction techniques". In some instances certain generic groups might be incompatible with the assembly illustrated in the procedures and schemes below and so will require the use of protecting groups. The use of protecting groups is well known in the art (see for example "*Protective Groups in Organic Synthesis*", T. W. Greene, P. G. M. Wuts, Wiley-Interscience, 1999).

The compounds of formula I can be obtained by:

a) deprotecting a compound of structure II

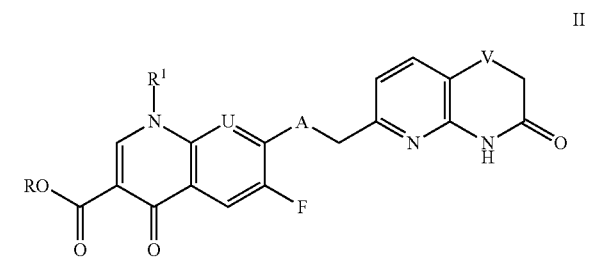

II wherein R represents alkyl, allyl or benzyl, using general reaction technique 1.

b) deprotecting a compound of structure III

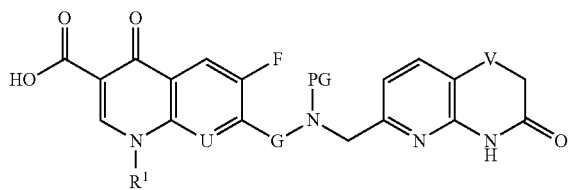

III wherein -G-N(PG)- corresponds to the group A such as for example $A^6$ (in which case the nitrogen atom which is protected with the group PG is the terminal nitrogen atom present in the —CH$_2$CH$_2$NH— group of $A^6$) and PG represents an amine protecting group such as Boc, Alloc or Cbz using general reaction technique 5.

c) reacting either a compound of structure IVa

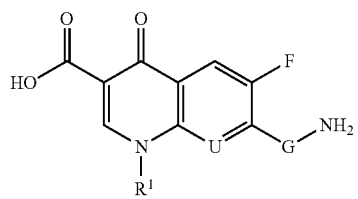

IVa wherein -G-NH— corresponds to the groups $A^1$, $A^3$, $A^4$, $A^5$, or $A^6$, or a compound of structure IVb

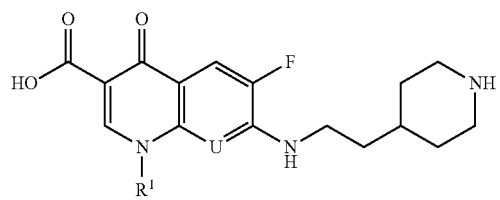

IVb with the compound of structure V

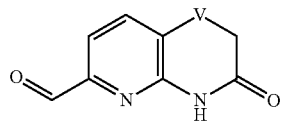

V using general reaction technique 2.

d) reacting the compound of structure VI

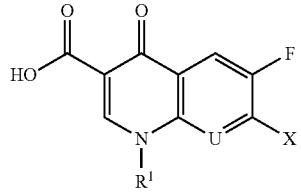

VI wherein X represents a halogen such as fluorine, chlorine or bromine, either with a compound of structure VIIa

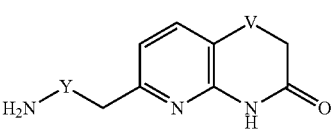

VIIa wherein the group —NH—Y— corresponds to the groups $A^1$ or $A^2$, or with a compound of structure VIIb

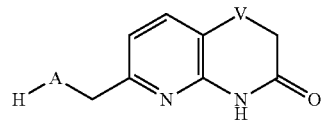

VIIb wherein the group A represents the groups $A^4$ or $A^6$ using general reaction technique 3.

e) reacting a compound of structure VIII

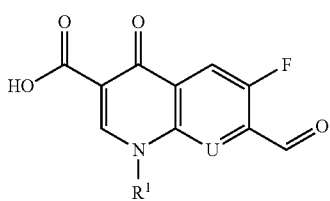

VIII with a compound of structure VIIa, using general reaction technique 2.

Preparation of the Synthesis Intermediates:
Compounds of Structure II:
Compounds of structure II can be obtained by
aa) reacting either a compound of structure IXa

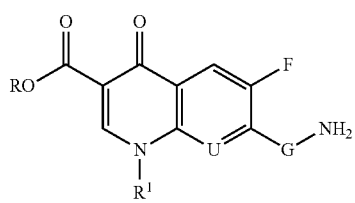

IXa wherein -G-NH— corresponds to the groups $A^1$, $A^3$, $A^4$, $A^5$ or $A^6$, and R represents alkyl, allyl or benzyl, or a compound of structure IXb

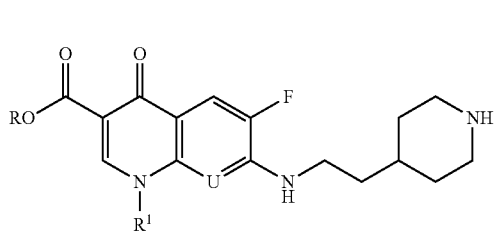

IXb with a compound of structure V, using general reaction technique 2.

bb) reacting a compound of structure X

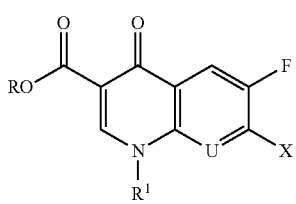

X wherein X represents halogen such as bromine or chlorine and R represents alkyl, allyl or benzyl with either a compound of structure VIIa or VIIb using general reaction technique 3.

cc) reacting a compound of structure XI

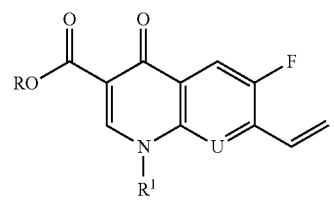

XI wherein R represents alkyl, allyl or benzyl with a compound of structure VIIb wherein A represents $A^4$ and E represents a bond,

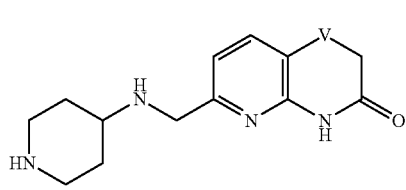

VIIb (wherein A = $A^4$; E = bond)

in presence of 1,1,3,3-tetramethylguanidine.

dd) deprotecting the ester function in a compound of structure XII

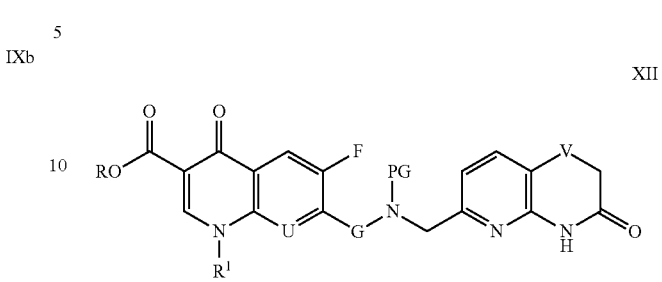

XII wherein -G-N(PG)- corresponds to A such as for example the group $A^6$ in which case the nitrogen atom which is protected with the group PG is the terminal nitrogen atom present in the —$CH_2CH_2NH$— group), PG represents an amine protecting group such as Boc, Alloc or Cbz and R represents alkyl, allyl or benzyl using an appropriate general reaction technique 1.

Compounds of Structures III and XII:

The compounds of structures III and XII can be prepared as described in the scheme 1 hereafter.

Scheme 1

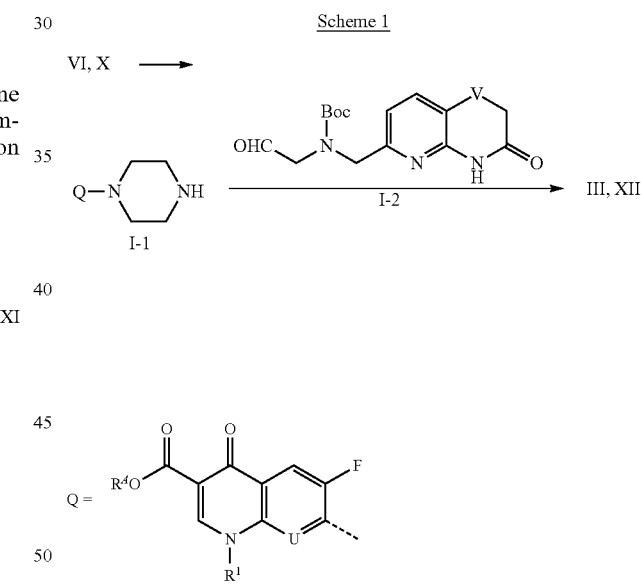

In Scheme 1, $R^4$ represents hydrogen, alkyl, allyl or benzyl.

The compounds of structures VI or X may be reacted with piperazine affording the intermediates of structure I-1 which can be further reacted with the compounds of structure I-2 using general reaction technique 2. Alternatively the compounds of structure III can be obtained from the compounds of structure XII using general reaction technique 1.

Compounds of Structures IVa, IVb, IXa, IXb, VIII and XI:

The compounds of structures IVa and IXa wherein -G-NH— corresponds to $A^4$ or $A^6$, and the compounds of structures IVb and IXb can be prepared as described in the scheme 2 hereafter.

Scheme 2

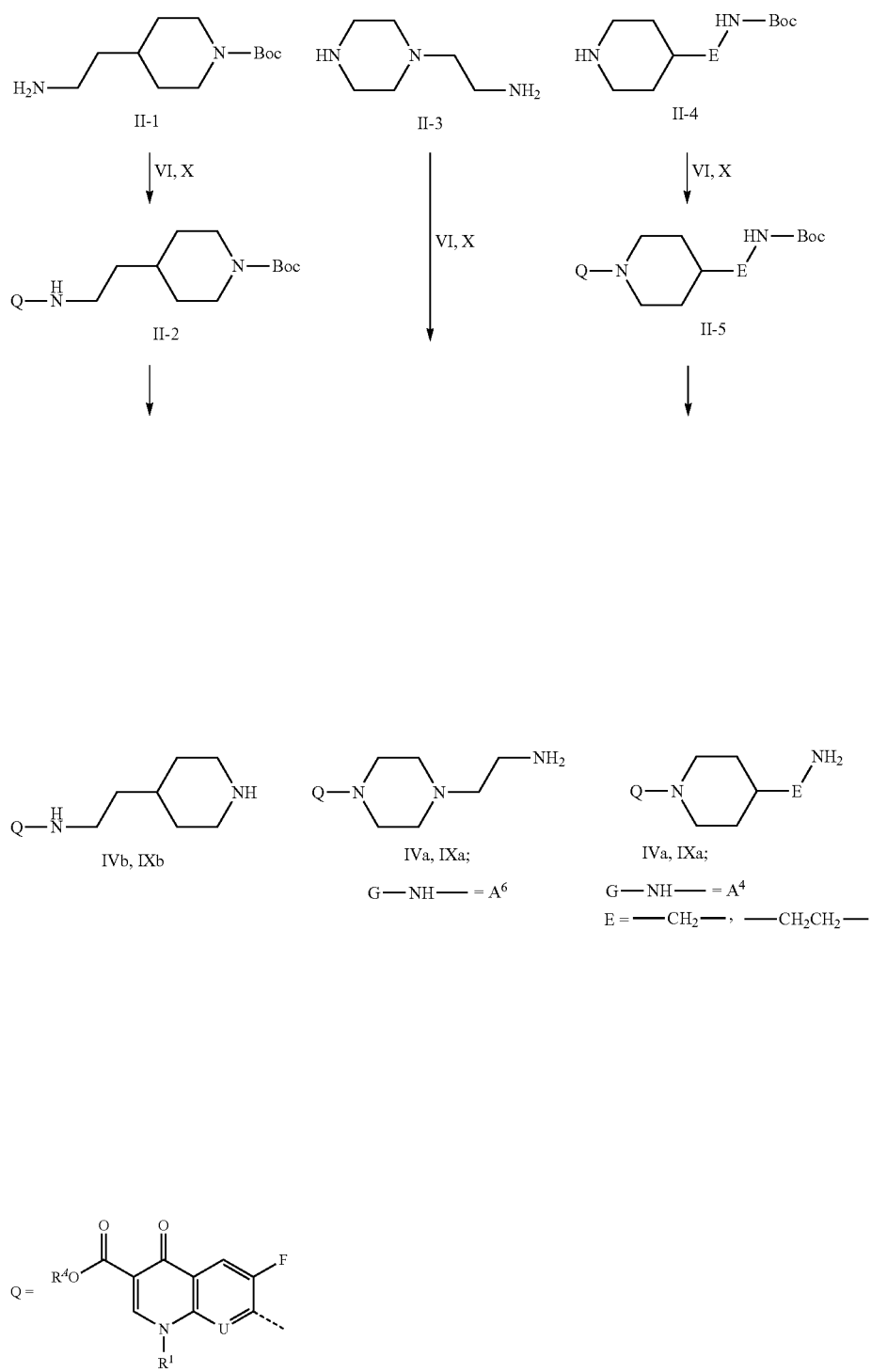

In Scheme 2, $R^A$ represents hydrogen, alkyl, allyl or benzyl.

The amino derivatives of structures II-1, II-3, and II-4 can be reacted with the quinolone or naphthyridinone derivatives of structures VI or X, using general reaction technique 3, affording after optional cleavage of the Boc protecting group using general reaction technique 5, the corresponding derivatives of structures IVa, and IXa wherein -G-NH— corresponds to $A^4$ or $A^6$ and the compounds of structures IVb and IXb.

The compounds of structures IVa and IXa wherein -G-NH represents the group $A^3$ and the compounds of structures VIII and XI can be prepared as described in the scheme 3 hereafter.

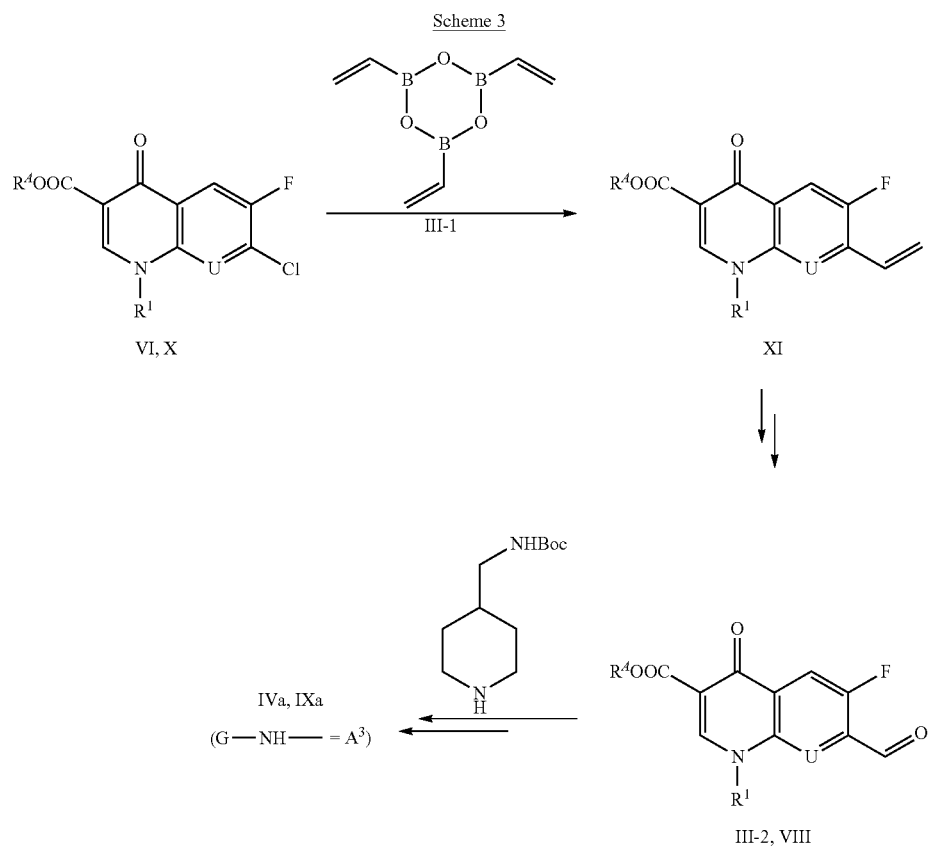

Scheme 3

In scheme 3, $R^A$ represents hydrogen, alkyl, allyl or benzyl.

The quinolone or naphthyridinone derivatives of structures VI or X may be reacted with vinyl boronic anhydride III-1 (complexed with pyridine) using general reaction technique 4, affording the derivatives of structure XI which can be sequentially transformed into their corresponding 1,2-diol homologues e.g. through osmium catalyzed 1,2-dihydroxylation and the corresponding aldehydes of structures III-2 ($R^A$=alkyl, allyl or benzyl) or VIII ($R^A$=hydrogen), e.g. through NaIO$_4$ cleavage. The aldehydes of structure III-2 can be reacted with tBu-N-(4-piperidinylmethyl)carbamate using general reaction technique 2 followed by removal of the Boc protecting group using general reaction technique 5, affording the compounds of structures IVa and IXa wherein -G-NH— corresponds to the group $A^3$.

Compounds of Structures V, VI and X

The compounds of structure V are prepared according to WO2002/056882. The compounds of structures VI and X are commercially available or can be prepared in analogy to EP 187376.

Compounds of Structures VIIa and VIIb:

The compounds of structure VIIa wherein the group —HN—Y— corresponds to the groups $A^1$ or $A^2$, or the compounds of structure VIIb wherein A represents $A^4$ or $A^6$, can be prepared as described in the scheme 4 hereafter.

Scheme 4

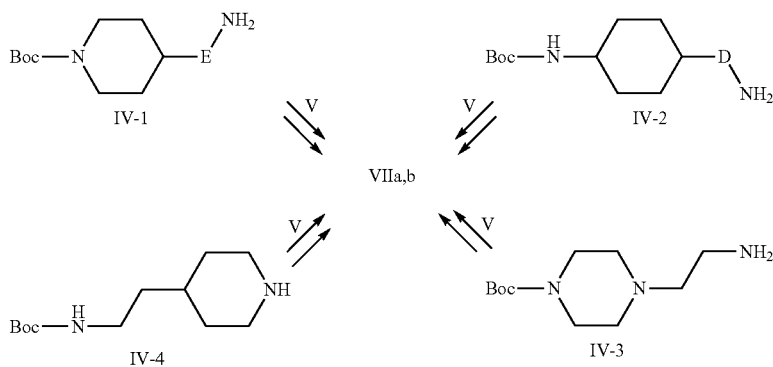

The amino derivatives of structures IV-1, IV-2, IV-3 and IV-4 can be sequentially reacted with the aldehyde derivatives of structure V using general reaction technique 2 and deprotected using general reaction technique 5, affording the derivatives of structure VIIa wherein -G-NH— corresponds to the groups $A^1$ or $A^2$, or the derivatives of structure VIIb wherein A represents $A^4$ or $A^6$.

Intermediates for the Synthesis of Compounds III, IVa-b, IXa-b, VIIa-b, VIII, XI and XII The compounds of structure 1-2 can be prepared as described in the scheme 5 hereafter.

Scheme 5

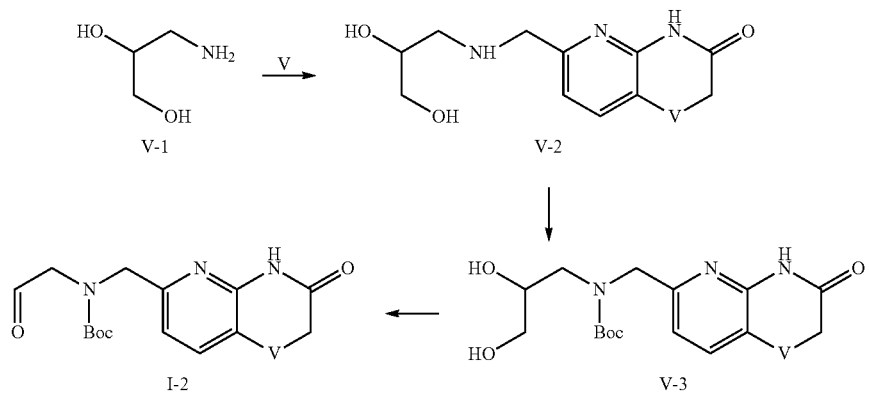

3-Aminopropane-1,2-diol can be reacted with the derivatives of structure V using general reaction technique 2, affording the diol derivatives of structure V-2 which may be further reacted with (Boc)$_2$O in presence of a bases such as NaHCO$_3$ or DMAP. The resulting derivatives of structure V-3 can be reacted with NaIO$_4$, affording the derivatives of structure I-2.

Experimental Part

All temperatures are stated in ° C. All temperatures are stated in ° C. Unless otherwise indicated, the reactions take place at rt.

Analytical TLC characterisations were performed with 0.2 mm plates: Merck, Silica gel 60 F$_{254}$. Elution is performed with EA, Hept, DCM, MeOH or mixtures thereof. Detection was done with UV or with a solution of KMnO$_4$ (3 g), K$_2$CO$_3$ (20 g), 5% NaOH (3 mL) and H$_2$O (300 mL) with subsequent heating.

CCs were performed using Brunschwig 60A silica gel (0.032-0.63 mm), elution being carried out with EA, Hept, DCM, MeOH or mixtures thereof. When the compounds contained an acid function, 1% of AcOH was added to the eluent(s). NH$_4$OH as used for CC is 25% aq.

Compounds were characterized by $^1$H-NMR (300 MHz) (Varian Oxford); or by $^1$H-NMR (400 MHz) (Bruker Advance 400). Chemical shifts δ are given in ppm relative to the solvent used; multiplicities: s=singlet, d=doublet, t=triplet, q=quadruplet, p=pentuplet, hex=hexet, hep=heptet, m=multiplet, br.=broad; coupling constants J are given in Hz. Alternatively compounds were characterized by LC-MS (Sciex API 2000 with Agilent 1100 Binary Pump with DAD and ELSD or an Agilent quadrupole MS 6140 with Agilent 1200 Binary Pump, DAD and ELSD); by TLC (TLC plates from Merck, Silica gel 60 F$_{254}$); or by melting point.

The analytical LC-MS data have been obtained using the following respective conditions:

MS1 data:
　Column: Zorbax SB-Aq, 3.5 lam, 4.6×50 mm;
　Injection volume: 1 μL;
　Column oven temperature: 40° C.;
　Detection: UV 210 nm, ELSD and MS;
　MS ionization mode: ESI+;
　Eluents: A: H$_2$O+0.04% TFA; and B: MeCN;
　Flow rate: 4.5 mL/min;
　Gradient: 5% B to 95% B (0.0 min-1.0 min), 95% B (1.0 min-1.45 min).

MS2 data:
　Column: Zorbax Extend C18, 5 μm, 4.6×50 mm;
　Injection volume: 5 μL;
　Column oven temperature: 40° C.;
　Detection: UV 210 nm, ELSD and MS;
　MS ionization mode: ESI−;
　Eluents: A: H$_2$O+0.04% NH$_3$; and B: MeCN;
　Flow rate: 4.5 mL/min;
　Gradient: 5% B to 95% B (0.0 min-0.75 min), 95% B (0.75 min-1.45 min).

The prep-HPLC purifications were performed on a Gilson HPLC system, equipped with a Gilson 215 autosampler, Gilson 333/334 pumps, Dionex MSQ Plus detector system, and a Dionex UVD340U (or Dionex DAD-3000) UV detector, using the following respective conditions:
　Column: Waters XBridge C18, 10 μm, 30×75 mm;
　Flow rate: 75 mL/min;
　Eluents: A: H$_2$O+0.5% NH$_4$OH; B: MeCN
　Gradient: 90% A to 5% A (0.0 min-3.5 min), 5% A (3.5 min-5.0 min).

Preparations:

Preparation A: trans-7-(4-Aminomethyl-cyclohexylamino)-1-cyclopropyl-6-fluoro-4-oxo-1,4-dihydro-[1,8]naphthyridine-3-carboxylic acid A.i. trans-4-(azidomethyl)cyclohexanamine hydrochloride A solution of N-[(trans)-4-(azidomethyl)cyclohexyl]-carbamic acid tert-butyl ester (305 mg; CAS 956352-36-6; prepared according to WO 2007/125952) in dioxane (5 mL) was treated with 4M HCl in dioxane (1.2 mL) and further stirred at rt overnight. The resulting solid was collected by filtration, washed with dry ether, affording 212 mg (93% yield) of a colorless solid.

MS1 (ESI, m/z): 196.40[M+MeCN+H$^+$]; $t_R$=0.40 min.

A.ii. trans-7-(4-azidomethyl-cyclohexylamino)-1-cyclopropyl-6-fluoro-4-oxo-1,4-dihydro-[1,8]naphthyridine-3-carboxylic acid A mixture of 7-chloro-1-cyclopropyl-6-fluoro-1,4-dihydro-4-oxo-1,8-naphthyridine-3-carboxylic acid (311 mg; CAS 100361-18-0; commercial) and intermediate A.i (210 mg) in MeCN (7 mL) was treated with DIPEA (0.58 mL) and heated at 70° C. overnight. The reaction mixture was cooled to rt and the solid was collected by filtration affording 365 mg (83% yield) of a yellow solid.

MS1 (ESI, m/z): 402.19 [M+H$^+$]; $t_R$=0.95 min.

A.iii. trans-7-(4-Aminomethyl-cyclohexylamino)-1-cyclopropyl-6-fluoro-4-oxo-1,4-dihydro-[1,8]naphthyridine-3-carboxylic acid A suspension of intermediate A.ii (360 mg) in THF (5 mL) was treated with PPh$_3$ (260 mg) and water (0.32 mL) and further stirred at 50° C. for 5 h. The reaction mixture was evaporated under reduced pressure and the residue was stirred in EA. The resulting solid was filtered washed with EA/MeOH, affording 365 mg (100% yield) of a colorless solid.

MS1 (ESI, m/z): 375.17 [M+H$^+$]; $t_R$=0.58 min.

Preparation B: trans-6-(((4-aminocyclohexyl)amino)methyl)-2H-pyrido[3,2-b][1,4]thiazin-3(4H)-one dihydrochloride B.i. trans-{4-[(3-Oxo-3,4-dihydro-2H-pyrido[3,2-b][1,4]thiazin-6-ylmethyl)-amino]-cyclohexyl}-carbamic acid tert-butyl ester A suspension of N-(trans-4-aminocyclohexyl)-carbamic acid tert-butyl ester (214 mg; CAS 177906-48-8; commercial) and 3,4-dihydro-3-oxo-2H-pyrido[3,2-b]-1,4-thiazine-6-carboxaldehyde (225 mg; CAS 443956-16-9; prepared according to WO 2002056882) in DCM/MeOH (6:1; 3.5 mL) was treated with NaHB(OAc)$_3$ (633 mg) and further stirred at rt for 5 h. The reaction mixture was diluted with DCM and water. The aq. layer was extracted with DCM/MeOH (9:1). The combined org. layers were washed with water and brine, dried over MgSO$_4$, filtered, evaporated under reduced pressure and purified by CC (DCM/MeOH 19:1 to 9:1+0.5% NH$_4$OH) affording 283 mg (72% yield) of a colorless solid.

MS1 (ESI, m/z): 393.35 [M+H$^+$]; $t_R$=0.65 min.

B.ii. trans-6-(((4-aminocyclohexyl)amino)methyl)-2H-pyrido[3,2-b][1,4]thiazin-3(4H)-one dihydrochloride Starting from intermediate B.i (279 mg) and proceeding in analogy to preparation A, step A.i, the title compound was obtained as a colorless solid (258 mg; 100% yield).

MS1 (ESI, m/z): 293.28 [M+H$^+$]; $t_R$=0.60 min.

Preparation C: benzyl 1-cyclopropyl-6-fluoro-4-oxo-7-vinyl-1,4-dihydro-1,8-naphthyridine-3-carboxylate C.i. benzyl 7-chloro-1-cyclopropyl-6-fluoro-4-oxo-1,4-dihydro-1,8-naphthyridine-3-carboxylate A suspension of 7-chloro-1-cyclopropyl-6-fluoro-1,4-dihydro-4-oxo-1,8-naphthyridine-3-carboxylic acid (2.83 g; commercial) in DMF (20 mL) was treated with benzyl bromide (1.31 mL) and K$_2$CO$_3$ (2.07 g) and heated at 65° C. for 24 h. The reaction mixture was poured on water and the resulting solid was filtered off, washed with water and EA, affording after drying 2.60 g (70% yield) of a colourless solid.

MS1 (ESI, m/z): 373.27 [M+H$^+$]; $t_R$=0.91 min.

C.ii. benzyl 1-cyclopropyl-6-fluoro-4-oxo-7-vinyl-1,4-dihydro-1,8-naphthyridine-3-carboxylate A mixture of intermediate C.i. (969 mg), vinylboronic anhydride pyridine complex (313 mg), tetrakis-(triphenylphosphine)-palladium (150 mg) and K$_2$CO$_3$ (431 mg) in H$_2$O (5 mL) and dioxane (13 mL) was degassed with argon and heated at reflux for 5 h. The mixture was allowed to cooled to rt, partitioned between water and EA/MeOH 9:1 and the solid was filtered off. The two layers were separated and the aq. phase was washed with EA/MeOH 9:1. The combined org. layers were washed with water and brine, dried over MgSO$_4$ and concentrated under reduced pressure and purified by CC (Hept/EA) affording 120 mg (13% yield) of impure material which was used as such.

MS1 (ESI, m/z): 365.32 [M+H$^+$]; $t_R$=0.93 min.

Preparation D: 6-((piperidin-4-ylamino)methyl)-2H-pyrido[3,2-b][1,4]thiazin-3(4H)-one D.i. 6 tert-butyl 4-(((3-oxo-3,4-dihydro-2H-pyrido[3,2-b][1,4]thiazin-6-yl)methyl)amino)piperidine-1-carboxylate Starting from 4-amino-1-Boc-piperidine (401 mg) and 3,4-dihydro-3-oxo-2H-pyrido[3,2-b]-1,4-thiazine-6-carboxaldehyde (450 mg; CAS 443956-16-9; prepared according to WO 2002/056882) and proceeding in analogy to preparation B step B.i, the title compound was obtained as a yellow foam (950 mg; quantitative yield).

MS1 (ESI, m/z): 379.36 [M+H$^+$]; $t_R$=0.59 min.

D.ii. 6-((piperidin-4-ylamino)methyl)-2H-pyrido[3,2-b][1,4]thiazin-3(4H)-one dihydrochloride Starting from intermediate D.i (757 mg) and proceeding in analogy to preparation A, step A.i, the title compound was obtained as a yellow solid (946 mg; quantitative yield).

MS1 (ESI, m/z): 279.32 [M+H$^+$]; $t_R$=0.30 min.

Preparation E: 7-(4-(2-aminoethyl)piperazin-1-yl)-1-cyclopropyl-6-fluoro-4-oxo-1,4-dihydro-1,8-naphthyridine-3-carboxylic acid Starting from 7-chloro-1-cyclopropyl-6-fluoro-1,4-dihydro-4-oxo-1,8-naphthyridine-3-carboxylic acid (424 mg; CAS 100361-18-0; commercial) and 1-piperazineethanamine (194 mg; CAS 140-31-8; commercial) and proceeding in analogy to preparation A, step A.ii, the title compound was obtained as a yellowish solid (655 mg; 100% yield).
MS1 (ESI, m/z): 376.13 [M−H$^+$]; $t_R$=0.48 min.

Preparation F: 7-(4-(2-aminoethyl)piperidin-1-yl)-1-cyclopropyl-6-fluoro-4-oxo-1,4-dihydro-1,8-naphthyridine-3-carboxylic acid hydrochloride F.i. 7-(4-(2-((tert-butoxycarbonyl)amino)ethyl)piperidin-1-yl)-1-cyclopropyl-6-fluoro-4-oxo-1,4-dihydro-1,8-naphthyridine-3-carboxylic acid Starting from 7-chloro-1-cyclopropyl-6-fluoro-1,4-dihydro-4-oxo-1,8-naphthyridine-3-carboxylic acid (565 mg; CAS 100361-18-0; commercial) and N-[2-(4-piperidinyl)ethyl]-carbamic acid tert-butyl ester (194 mg; CAS 165528-81-4; commercial) and proceeding in analogy to preparation A, step A.ii, the title compound was obtained as a colorless solid (664 mg; 70% yield).
MS1 (ESI, m/z): 279.32 [M+H$^+$]; $t_R$=0.30 min.

F.ii. 7-(4-(2-aminoethyl)piperidin-1-yl)-1-cyclopropyl-6-fluoro-4-oxo-1,4-dihydro-1,8-naphthyridine-3-carboxylic acid hydrochloride Starting from intermediate F.i (650 mg) and proceeding in analogy to preparation A, step A.i, the title compound was obtained as a slightly yellow solid (571 mg; 100% yield).
MS1 (ESI, m/z): 375.18 [M+H$^+$]; $t_R$=0.60 min.

Preparation G: 1-cyclopropyl-6-fluoro-4-oxo-7-((2-(piperidin-4-yl)ethyl)amino)-1,4-dihydro-1,8-naphthyridine-3-carboxylic acid hydrochloride G.i. 7-((2-(1-(tert-butoxycarbonyl)piperidin-4-yl)ethyl)amino)-1-cyclopropyl-6-fluoro-4-oxo-1,4-dihydro-1,8-naphthyridine-3-carboxylic acid Starting from 7-chloro-1-cyclopropyl-6-fluoro-1,4-dihydro-4-oxo-1,8-naphthyridine-3-carboxylic acid (311 mg; CAS 100361-18-0; commercial) and 4-(2-aminoethyl)-1-piperidinecarboxylic acid tert-butyl ester (194 mg; CAS 146093-46-1; commercial) and proceeding in analogy to preparation A, step A.ii, the title compound was obtained as a colorless solid (240 mg; 46% yield).
MS1 (ESI, m/z): 475.27 [M+H$^+$]; $t_R$=0.95 min.

G.ii. 1-cyclopropyl-6-fluoro-4-oxo-7-((2-(piperidin-4-yl)ethyl)amino)-1,4-dihydro-1,8-naphthyridine-3-carboxylic acid hydrochloride Starting from intermediate G.i (237 mg) and proceeding in analogy to preparation A, step A.i, the title compound was obtained as a colorless solid (235 mg; 100% yield).
MS1 (ESI, m/z): 375.17 [M+H$^+$]; $t_R$=0.57 min.

Preparation H: 6-(((piperidin-4-ylmethyl)amino)methyl)-2H-pyrido[3,2-b][1,4]thiazin-3(4H)-one hydrochloride H.i. tert-butyl 4-((((3-oxo-3,4-dihydro-2H-pyrido[3,2-b][1,4]thiazin-6-yl)methyl)amino)methyl)piperidine-1-carboxylate Starting from 1-Boc-(4-aminomethyl)piperidine (214 mg) and 3,4-dihydro-3-oxo-2H-pyrido[3,2-b]-1,4-thiazine-6-carboxaldehyde (225 mg; CAS 443956-16-9; prepared according to WO 2002/056882) and proceeding in analogy to preparation B step B.i, the title compound was obtained as a yellow foam (387 mg; 98% yield).
MS1 (ESI, m/z): 393.34 [M+H$^+$]; $t_R$=0.62 min.

H.ii. 6-(((piperidin-4-ylmethyl)amino)methyl)-2H-pyrido[3,2-b][1,4]thiazin-3(4H)-one hydrochloride Starting from intermediate H.i (381 mg) and proceeding in analogy to preparation A, step A.i, the title compound was obtained as a yellowish solid (395 mg; quantitative yield).
MS1 (ESI, m/z): 293.29 [M+H$^+$]; $t_R$=0.35 min.

Preparation I: 7-((4-(aminomethyl)piperidin-1-yl)methyl)-1-cyclopropyl-6-fluoro-4-oxo-1,4-dihydro-1,8-naphthyridine-3-carboxylic acid hydrochloride I.i. 1-cyclopropyl-6-fluoro-4-oxo-7-vinyl-1,4-dihydro-1,8-naphthyridine-3-carboxylic acid Starting from 7-chloro-1-cyclopropyl-6-fluoro-1,4-dihydro-4-oxo-1,8-naphthyridine-3-carboxylic acid (4.23 g; commercial) and vinylboronic anhydride pyridine complex (1.80 g, commercial) and proceeding in analogy to preparation C, step C.ii, the title compound was obtained as a yellowish solid (1.99 g; crude material, 50% yield).
$^1$H NMR (DMSO d-6) δ: 8.81 (s, 1H), 8.48 (d, J=9.4 Hz, 1H), 7.18 (ddd, J$_1$=17.1 Hz, J$_2$=10.7 Hz, J$_3$=1.6 Hz, 1H), 6.76 (dd, J$_1$=17.1 Hz, J$_2$=1.9 Hz, 1H), 5.97 (dd, J$_1$=10.7 Hz, J$_2$=1.9 Hz, 1H), 3.87 (m, 1H), 1.20 (m, 4H)

I.ii. 1-cyclopropyl-7-(1,2-dihydroxyethyl)-6-fluoro-4-oxo-1,4-dihydro-1,8-naphthyridine-3-carboxylic acid A solution of intermediate I.i (1.67 g) in DCM/H$_2$O (3:1; 61 mL) was treated with NMO (989 mg) and K$_2$OsO$_4$. 2H$_2$O (22.5 mg) and vigorously stirred at rt overnight. The reaction mixture was partitioned between water and DCM/MeOH (9:1). The org layer was separated. The aq. layer was washed with DCM/MeOH (9:1) and the combined org. layers were washed with brine, dried over MgSO$_4$ and concentrated under reduced pressure. The residue was triturated with EA/ether, filtered, washed with EA/ether and dried under HV affording 1.53 g (81% yield) as a beige solid.
MS1 (ESI, m/z): 309.09 [M+H$^+$]; $t_R$=0.53 min.

I.iii. 1-cyclopropyl-6-fluoro-7-formyl-4-oxo-1,4-dihydro-1,8-naphthyridine-3-carboxylic acid A suspension of intermediate I.ii (1.54 g) in acetone (30 mL) was treated with a solution of NaIO$_4$ (2.46 g) in water (20 mL). The mixture was stirred at rt overnight. The reaction mixture was filtered and the filtrate was concentrated under reduced pressure. The residue was partitioned between DCM/MeOH (9:1) and water. The two phases were separated and org. layer washed with brine, dried over MgSO$_4$, filtered and concentrated. The residue was triturated with EA/ether, filtered, washed with EA/ether and dried under HV affording 270 mg (20% yield) of a yellowish solid.
MS1 (ESI, m/z): 295.08 [M+H$_2$O+H$^+$]; $t_R$=0.53 min.

I.iv. 7-((4-(((tert-butoxycarbonyl)amino)methyl)piperidin-1-yl)methyl)-1-cyclopropyl-6-fluoro-4-oxo-1,4-dihydro-1,8-naphthyridine-3-carboxylic acid Starting from intermediate I.iii (230 mg) and tert-butyl N-(4-piperidinylmethyl)carbamate (107 mg, commercial)

and proceeding in analogy to preparation B, step B.i, the title compound was obtained as a grey solid (60 mg; 25% yield).
MS1 (ESI, m/z): 475.29 [M+H$^+$]; $t_R$=0.54 min.

I.v. 7-((4-(aminomethyl)piperidin-1-yl)methyl)-1-cyclopropyl-6-fluoro-4-oxo-1,4-dihydro-1,8-naphthyridine-3-carboxylic acid hydrochloride A solution of intermediate I.iv (57 mg) in dioxane (0.6 mL) was treated with 4M HCl in dioxane (0.12 mL) and further stirred at rt for 24 h. The solid was collected by filtration, washed with ether and DCM and dried under HV, affording 47 mg (99% yield) of a grey solid.
MS1 (ESI, m/z): 375.14 [M+H$^+$]; $t_R$=0.38 min Preparation J: tert-butyl((3-oxo-3,4-dihydro-2H-pyrido[3,2-b][1,4]thiazin-6-yl)methyl)(2-oxoethyl)carbamate J.i. rac-(2,3-Dihydroxy-propyl)-(3-oxo-3,4-dihydro-2H-pyrido[3,2-b][1,4]thiazin-6-ylmethyl)-carbamic acid tert-butyl ester A mixture of 3-amino-1,2-propanediol (0.24 mL) and 3,4-dihydro-3-oxo-2H-pyrido[3,2-b]-1,4-thiazine-6-carboxaldehyde (583 mg; CAS 443956-16-9; prepared according to WO2002/056882) in DCM/EtOH (1:1; 20 mL) was treated with AcOH (3 drops) and stirred at rt for 5 h. NaBH$_4$ (113 mg) was added at 0° C. and stirring was continued for 30 min. The reaction mixture was quenched by dropwise addition of 1N HCl, then neutralized with sat aq. NaHCO$_3$, treated with BOC$_2$O (1.31 g) and further stirred at rt for 2 days. The mixture was partitioned between DCM and a sat aq NaHCO$_3$ solution. The org layer was dried over MgSO$_4$, concentrated under reduced pressure and the residue was purified by CC (EA to EA/MeOH 9:1), affording 1.37 g (quantitative yield) of a yellowish foam.
MS1 (ESI, m/z): 370.07 [M+H$^+$]; $t_R$=0.64 min.

J.ii. tert-butyl((3-oxo-3,4-dihydro-2H-pyrido[3,2-b][1,4]thiazin-6-yl)methyl)(2-oxoethyl)carbamate A solution of intermediate J.i (1.11 g) in acetone (12 mL) was treated dropwise with a solution of NaIO$_4$ (802 mg) in water (6 mL). The mixture was stirred at rt for 30 min. The solid was filtered off and washed with EA. The org. layer was washed with diluted brine, dried over MgSO$_4$ and concentrated under reduced pressure, affording 730 mg (72% yield) of a yellow foam which was directly used in the next step.
MS1 (ESI, m/z): 282.00 [M+H$^+$]; $t_R$=0.64-0.75 min (broad).

Preparation K: trans-4-azidomethyl-cyclohexylamine

K.i. tert-butyl(trans-4-(azidomethyl)cyclohexyl)carbamate

Sodium azide (1.64 g) was added to a solution of N-[trans-4-[[(methylsulfonyl)oxy]methyl]cyclohexyl]-carbamic acid tert-butyl ester (7.1 g, CAS 683269-95-6; prepared according to WO 2012/101013) in DMF (80 mL). The suspension was stirred at 55° C. for 4 h. The reaction mixture was allowed to cool to rt and diluted with water and EA. The two phases were separated. The aq. phase was extracted twice with EA. The combined org. layers were washed with water (2×) and brine, dried over MgSO$_4$ and concentrated under reduced pressure. The residue was purified by CC (Hept/EA) affording the title compound (4.15 g, 71%) as a colourless solid.
$^1$H NMR (CDCl$_3$) δ: 4.32-4.48 (m, 1H), 3.24-3.44 (m, 1H), 3.12 (d, J=6.7 Hz, 2H), 1.96-2.10 (m, 2H), 1.73-1.86 (m, 2H), 1.42 (s, 9H), 0.97-1.17 (m, 4H).

K.ii. trans 4-Azidomethyl-cyclohexylamine

To a solution of Preparation K.i (4.1 g) in dioxane (81 mL) was added 4M HCl in dioxane (31 mL) dropwise. The reaction mixture was stirred at rt overnight. The mixture was concentrated under reduced pressure and the residue was partitioned between water and DCM/MeOH (9:1). The two phases were separated. The organic phase was discarded. The aqueous layer was basified with NH$_4$OH to pH 9 and washed 3 times with DCM/MeOH (9:1). The combined organic phases were dried over MgSO$_4$, filtered and concentrated under reduced pressure to give the title compound (1.82 g, 73% yield) as a yellow liquid which was used as such.
$^1$H NMR (CDCl$_3$) δ: 3.13 (d, J=6.6 Hz, 2H), 2.50-2.68 (m, 1H), 1.69-1.96 (m, 4H), 1.38-1.60 (m, 1H), 0.92-1.19 (m, 4H).

Preparation L: trans-7-(4-aminomethyl-cyclohexylamino)-6-fluoro-1-methyl-4-oxo-1,4-dihydro-[1,8]naphthyridine-3-carboxylic acid L.i. trans-7-(4-Azidomethyl-cyclohexylamino)-6-fluoro-1-methyl-4-oxo-1,4-dihydro-[1,8]naphthyridine-3-carboxylic acid A mixture of 7-chloro-6-fluoro-1,4-dihydro-1-methyl-4-oxo-1,8-naphthyridine-3-carboxylic acid, (513 mg; CAS 1279121-43-5 prepared according to WO 2011/037433) and product of preparation K (308 mg) and DIPEA (0.72 mL) in MeCN (10 mL) was heated at 70° C. overnight. The reaction mixture was filtered and the solid and was washed with MeCN. The mother liquor was evaporated under reduced pressure and the residue was stirred with MeCN/ether/MeOH and the solid was collected by filtration. The two crops were combined and dried under reduced pressure to afford 684 mg (91% yield) of a yellow solid
$^1$H NMR (DMSO) δ: 8.85 (s, 1H), 8.14 (d, J=7.3 Hz, 1H), 7.91 (d, J=10.6 Hz, 1H), 3.91 (s, 3H), 3.25 (d, J=6.4 Hz, 2H), 1.94-2.07 (m, 2H), 1.74-1.86 (m, 2H), 1.33-1.61 (overlapped m, 2H), 1.21-1.30 (m, 2H), 1.04-1.20 (m, 2H).

L.ii. trans-7-(4-aminomethyl-cyclohexylamino)-6-fluoro-1-methyl-4-oxo-1,4-dihydro-[1,8]naphthyridine-3-carboxylic acid PPh$_3$ (505 mg) and water (0.63 mL) were added to a suspension of intermediate L.i (655 mg) in THF (10.5 mL) and the mixture was heated at 50° C. for 5 h. The volatiles were removed under reduced pressure and the residue was stirred in EA/MeOH. The solid was collected by filtration, washed with EA/MeOH and dried under HV affording 587 mg of a whitish powder (96% yield).
$^1$H NMR (DMSO) δ: 8.84 (s, 1H), 8.11 (d, J=7.3 Hz, 1H), 7.89 (d, J=10.7 Hz, 1H), 3.83-4.05 (overlapped m, 1H), 3.90 (s, 3H), 2.40 (d, J=6.1 Hz, 2H), 1.92-2.05 (m, 2H), 1.76-1.89 (m, 2H), 1.29-1.50 (m, 2H), 1.10-1.29 (m, 1H), 0.89-1.10 (m, 2H).

Preparation M: trans-7-(4-Aminomethyl-cyclohexylamino)-1-ethyl-6-fluoro-4-oxo-1,4-dihydro-[1,8]naphthyridine-3-carboxylic acid M.i. trans-7-(4-Azidomethyl-cyclohexylamino)-1-ethyl-6-fluoro-4-oxo-1,4-dihydro-[1,8]naphthyridine-3-carboxylic acid A mixture of 7-chloro-1-ethyl-6-fluoro-1,4-dihydro-4-oxo-1,8-naphthyridine-3-carboxylic acid (4.51 mg; CAS 79286-73; prepared according to EP 27752), compound of preparation K (46.3 mg) and DIPEA (0.108 mL) in MeCN (1.5 mL) was heated at 70° C. overnight. The mixture was cooled to rt and diluted with water. The resulting solid was filtered and stirred in EA affording 105 mg (91% yield) of brownish solid. The product was used as such in the next step.
$^1$H NMR (DMSO) δ: 8.88 (s, 1H), 8.16 (d, J=8.2 Hz, 1H), 7.91 (d, J=10.6 Hz, 1H), 4.46 (q, J=7.0 Hz, 2H), 3.83-4.02 (m, 1H), 3.25 (d, J=6.4 Hz, 2H), 1.92-2.06 (m, 2H), 1.73-1.88 (m, 2H), 1.31-1.62 (m, 3H), 1.36 (t, J=7.0 Hz, 3H), 1.04-1.23 (m, 2H).

M.ii. trans-7-(4-Aminomethyl-cyclohexylamino)-1-ethyl-6-fluoro-4-oxo-1,4-dihydro-[1,8]naphthyridine-3-carboxylic acid PPh$_3$ (72 mg) and water (0.108 mL) were added to a suspension of intermediate M.i (97 mg) in THF (1.8 mL). The reaction mixture was heated at 50° C. for 5 h, allowed to reach rt and evaporated under reduced pressure. The residue was stirred with EA/MeOH, filtered, washed with EA/MeOH and dried under HV affording 90 mg (100% yield) of a beige solid. The product was used as such in the next step.
MS1 (ESI, m/z): 362.99 [M+H$^+$]; t$_R$=0.57 min.

Preparation N 7-[4-(2-Amino-ethyl)-piperidin-1-yl]-6-fluoro-1-methyl-4-oxo-1,4-dihydro-[1,8]naphthyridine-3-carboxylic acid N.i 7-(4-(2-((tert-butoxycarbonyl)amino)ethyl)piperidin-1-yl)-6-fluoro-1-methyl-4-oxo-1,4-dihydro-1,8-naphthyridine-3-carboxylic acid A mixture of 7-chloro-6-fluoro-1,4-dihydro-1-methyl-4-oxo-1,8-naphthyridine-3-carboxylic acid (228 mg; CAS 1279121-43-5 prepared according to WO 2011037433), 4-(2-Boc-aminoethyl)piperidine (203 mg, commercial) and DIPEA (0.32 mL) in MeCN (5.34 mL) was heated at 70° C. overnight. The mixture was cooled to rt, the precipitate was filtered off, washed with MeCN and dried under HV affording 248 mg (62% yield) of a white solid.
MS1 (ESI, m/z): 448.98 [M+H$^+$]; t$_R$=0.92 min.

N.ii. 7-[4-(2-Amino-ethyl)-piperidin-1-yl]-6-fluoro-1-methyl-4-oxo-1,4-dihydro-[1,8]naphthyridine-3-carboxylic acid To a suspension of intermediate N.i (238 mg) in dioxane (2 mL) was added dropwise 4M HCl in dioxane (0.53 mL). The reaction mixture was stirred at rt for 5 h, diluted with H$_2$O and EA/MeOH (9:1). The two phases were separated and the aq. phase was washed twice with EA/MeOH. The pH of the aq. phase was brought to pH~7 by addition of NH$_4$OH and the solution was concentrated under reduced pressure. The residue was stirred with DCM/MeOH (4:1),filtered and purified by HPLC (basic), affording 170 mg (92%) of a light yellow solid.
MS1 (ESI, m/z): 348.97 [M+H$^+$]; t$_R$=0.57 min.

EXAMPLES

Example 1 trans-1-Cyclopropyl-6-fluoro-4-oxo-7-(4-{[(3-oxo-3,4-dihydro-2H-pyrido[3,2-b][1,4]thiazin-6-ylmethyl)-amino]-methyl}-cyclohexylamino)-1,4-dihydro-[1,8]naphthyridine-3-carboxylic acid A suspension of compound of preparation A (60 mg) and 3,4-dihydro-3-oxo-2H-pyrido[3,2-b]-1,4-thiazine-6-carboxaldehyde (36 mg; CAS 443956-16-9; prepared according to WO 2002056882) in DCM/MeOH (4:1; 0.6 mL) was treated with NaHB(OAc)$_3$ (101 mg) and further stirred at rt for 5 h. The reaction mixture was diluted with DCM and water. The aq. layer was extracted with DCM/MeOH (9:1). The combined org. layers were washed with water and brine, dried over MgSO$_4$, filtered, evaporated under reduced pressure and purified by prep HPLC affording 47 mg (53% yield) of a colourless solid.
MS1 (ESI, m/z): 553.27 [M+H$^+$]; t$_R$=0.66 min.

Example 2 trans-1-Cyclopropyl-6-fluoro-4-oxo-7-{4-[(3-oxo-3,4-dihydro-2H-pyrido[3,2-b][1,4]thiazin-6-ylmethyl)-amino]-cyclohexylamino}-1,4-dihydro-[1,8]naphthyridine-3-carboxylic acid A mixture of 7-chloro-1-cyclopropyl-6-fluoro-1,4-dihydro-4-oxo-1,8-naphthyridine-3-carboxylic acid (82 mg; CAS 100361-18-0; commercial) and intermediate B (110 mg) in NMP (1.8 mL) was treated with DIPEA (0.27 mL) and heated at 100° C. for 4 h. The reaction mixture was cooled to rt, diluted with ether and the solid was collected by filtration, affording after purification by prep HPLC 5 mg (3% yield) of a beige solid.
MS2 (ESI, m/z): 537.18 [M−H$^+$]; t$_R$=0.52 min.

Example 3

1-Cyclopropyl-6-fluoro-4-oxo-7-(2-{4-[(3-oxo-3,4-dihydro-2H-pyrido[3,2-b][1,4]thiazin-6-ylmethyl)-amino]-piperidin-1-yl}-ethyl)-1,4-dihydro-[1,8]naphthyridine-3-carboxylic acid 3.i. 1-Cyclopropyl-6-fluoro-4-oxo-7-(2-{4-[(3-oxo-3,4-dihydro-2H-pyrido[3,2-b][1,4]thiazin-6-ylmethyl)-amino]-piperidin-1-yl}-ethyl)-1,4-dihydro-[1,8]naphthyridine-3-carboxylic acid benzyl ester A suspension of intermediate C (109 mg), intermediate D (105 mg) and TEA (0.1 mL) in DMF (0.6 mL) was treated with 1,1,3,3-tetramethylguanidine (0.01 mL) and further stirred at 90° C. for 6 h. The reaction mixture was allowed to reach rt, diluted with water and extracted with EA/MeOH (9:1; 3×). The combined org. layers were washed with water and brine, dried over MgSO$_4$, filtered, evaporated under reduced pressure and purified by CC (DCM/MeOH, 19:1 to 9:1), affording 70 mg (36% yield) of a slightly brown foam.
MS1 (ESI, m/z): 643.35 [M+H$^+$]; t$_R$=0.60 min.

3.ii. 1-Cyclopropyl-6-fluoro-4-oxo-7-(2-{4-[(3-oxo-3,4-dihydro-2H-pyrido[3,2-b][1,4]thiazin-6-ylmethyl)-amino]-piperidin-1-yl}-ethyl)-1,4-dihydro-[1,8]naphthyridine-3-carboxylic acid A solution of intermediate 3.i (64 mg) in AcOH (0.8 mL) and HBr (62% aqueous; 0.05 mL) was stirred at rt overnight. The reaction mixture was diluted with DCM/MeOH (9:1) and diluted aq. NH$_4$OH. The org layer was separated and the aq layer was extracted with DCM/MeOH (9:1). The combined org. layers were washed with brine, dried over MgSO$_4$, filtered, evaporated under reduced pressure and purified by prep HPLC affording 4 mg (7% yield) of a colorless solid.
MS1 (ESI, m/z): 553.24 [M+H$^+$]; $t_R$=0.50 min.

Example 4

1-Cyclopropyl-6-fluoro-4-oxo-7-(4-{2-[(3-oxo-3,4-dihydro-2H-pyrido[3,2-b][1,4]thiazin-6-ylmethyl)-amino]-ethyl}-piperazin-1-yl)-1,4-dihydro-[1,8]naphthyridine-3-carboxylic acid Starting from intermediate E (75 mg) and 3,4-dihydro-3-oxo-2H-pyrido[3,2-b]-1,4-thiazine-6-carboxaldehyde (45 mg; CAS 443956-16-9; prepared according to WO 2002056882) and proceeding in analogy to example 1 the title compound was obtained as yellowish solid (40 mg; 36% yield).
MS2 (ESI, m/z): 552.17 [M−H$^+$]; $t_R$=0.50 min.

Example 5

1-Cyclopropyl-6-fluoro-4-oxo-7-(4-{2-[(3-oxo-3,4-dihydro-2H-pyrido[3,2-b][1,4]thiazin-6-ylmethyl)-amino]-ethyl}-piperidin-1-yl)-1,4-dihydro-[1,8]naphthyridine-3-carboxylic acid Starting from intermediate F (66 mg) and 3,4-dihydro-3-oxo-2H-pyrido[3,2-b]-1,4-thiazine-6-carboxaldehyde (36 mg; CAS 443956-16-9; prepared according to WO 2002056882) and proceeding in analogy to example 1 the title compound was obtained as colourless solid (49 mg; 55% yield).
MS1 (ESI, m/z): 553.27 [M+H$^+$]; $t_R$=0.68 min.

Example 6

1-Cyclopropyl-6-fluoro-4-oxo-7-{2-[1-(3-oxo-3,4-dihydro-2H-pyrido[3,2-b][1,4]thiazin-6-ylmethyl)-piperidin-4-yl]-ethylamino}-1,4-dihydro-[1,8]naphthyridine-3-carboxylic acid Starting from intermediate G (72 mg) and 3,4-dihydro-3-oxo-2H-pyrido[3,2-b]-1,4-thiazine-6-carboxaldehyde (36 mg; CAS 443956-16-9; prepared according to WO 2002056882) and proceeding in analogy to example 1 the title compound was obtained as yellowish solid (37 mg; 42% yield).
MS1 (ESI, m/z): 553.32 [M+H$^+$]; $t_R$=0.65 min.

Example 7

1-Cyclopropyl-6-fluoro-4-oxo-7-(4-{[(3-oxo-3,4-dihydro-2H-pyrido[3,2-b][1,4]thiazin-6-ylmethyl)-amino]-methyl}-piperidin-1-yl)-1,4-dihydro-[1,8]naphthyridine-3-carboxylic acid A mixture of 7-chloro-1-cyclopropyl-6-fluoro-1,4-dihydro-4-oxo-1,8-naphthyridine-3-carboxylic acid (127 mg; CAS 100361-18-0; commercial) and intermediate H (168 mg) in MeCN (3 mL) was treated with DIPEA (0.27 mL) and heated at 70° C. for 3 h. The reaction mixture was cooled to rt and the solid was collected by filtration affording 202 mg (83% yield) of a colourless solid.
MS2 (ESI, m/z): 537.12 [M−H$^+$]; $t_R$=0.53 min.

Example 8 trans-1-Cyclopropyl-6-fluoro-4-oxo-7-(4-{[(3-oxo-3,4-dihydro-2H-pyrido[3,2-b][1,4]oxazin-6-ylmethyl)-amino]-methyl}-cyclohexylamino)-1,4-dihydro-[1,8]naphthyridine-3-carboxylic acid Starting from intermediate A (45 mg) and 3,4-dihydro-3-oxo-2H-pyrido[3,2-b]-1,4-oxazine-6-carboxaldehyde (27 mg; CAS 443956-11-4; prepared according to WO2002/056882) and proceeding in analogy to example 1 the title compound was obtained as colourless powder (27 mg; 34% yield).
MS1 (ESI, m/z): 537.24 [M+H$^+$]; $t_R$=0.65 min.

Example 9

1-Cyclopropyl-6-fluoro-4-oxo-7-(4-{[(3-oxo-3,4-dihydro-2H-pyrido[3,2-b][1,4]thiazin-6-ylmethyl)-amino]-methyl}-piperidin-1-ylmethyl)-1,4-dihydro-[1,8]naphthyridine-3-carboxylic acid Starting from intermediate I (45 mg) and 3,4-dihydro-3-oxo-2H-pyrido[3,2-b]-1,4-thiazine-6-carboxaldehyde (25 mg; CAS 443956-16-9; prepared according to WO2002/056882) and proceeding in analogy to example 1 the title compound was obtained as colourless powder (15 mg; 25% yield).
MS1 (ESI, m/z): 553.20 [M+H$^+$]; $t_R$=0.48 min.

Example 10

1-Cyclopropyl-6-fluoro-4-oxo-7-{4-[(3-oxo-3,4-dihydro-2H-pyrido[3,2-b][1,4]thiazin-6-ylmethyl)-amino]-piperidin-1-yl}-1,4-dihydro-[1,8]naphthyridine-3-carboxylic acid Starting from intermediate D (337 mg) and 7-chloro-1-cyclopropyl-6-fluoro-1,4-dihydro-4-oxo-1,8-naphthyridine-3-carboxylic acid (240 mg; CAS 100361-18-0; commercial) and proceeding in analogy to example 7 the title compound was obtained as yellowish solid (342 mg; 77% yield).
MS1 (ESI, m/z): 525.22 [M+H$^+$]; $t_R$=0.65 min.

Example 11

1-Cyclopropyl-6-fluoro-4-oxo-7-(4-{2-[(3-oxo-3,4-dihydro-2H-pyrido[3,2-b][1,4]thiazin-6-ylmethyl)-amino]-ethyl}-piperazin-1-yl)-1,4-dihydro-quinoline-3-carboxylic acid A suspension of 1-cyclopropyl-6-fluoro-1,4-dihydro-4-oxo-7-(1-piperazinyl)-3-quinolinecarboxylic acid (133 mg; CAS 85721-33-1; commercial) and intermediate J (135 mg) in DCM/MeOH (3:1; 4 mL) was treated with NaHB(OAc)$_3$ (170 mg) and further stirred at rt for 30 min. The reaction mixture was partitioned between DCM and a sat aq NaHCO$_3$ solution. The aq layer was extracted with DCM. The combined org layer were dried over MgSO$_4$ and concentrated under reduced pressure. The residue was dissolved in dioxane (2 mL), treated with 4N HCl in dioxane (1 mL) and further stirred at rt overnight. The reaction mixture was diluted with dioxane, filtered. The residue was dissolved in sat aq NaHCO$_3$ and DCM/MeOH (9:1), the org layer dried over MgSO$_4$ and concentrated under reduced pressure affording after crystallization from EA/MeOH 88 mg (40% yield) of a yellowish solid.

MS1 (ESI, m/z): 553.23 [M+H$^+$]; t$_R$=0.56 min.

Example 12

1-Cyclopropyl-6-fluoro-4-oxo-7-(4-{2-[(3-oxo-3,4-dihydro-2H-pyrido[3,2-b][1,4]oxazin-6-ylmethyl)-amino]-ethyl}-piperazin-1-yl)-1,4-dihydro-[1,8] naphthyridine-3-carboxylic acid Starting from the compound of Preparation E (75 mg) and 3-oxo-3,4-dihydro-2H-pyrido[3,2-b][1,4]oxazine-6-carboxaldehyde (36 mg; CAS 443956-11-4; commercial) and proceeding in analogy to example 1, the title compound was obtained, after purification by prep-HPLC, as a colorless solid (30 mg; 30% yield).

$^1$H NMR (DMSO) δ: 8.59 (s, 1H), 8.05 (d, J=13.6 Hz, 1H), 7.28 (d, J=8.1 Hz, 1H), 6.98 (d, J=8.1 Hz, 1H), 4.59 (s, 2H), 3.80-3.91 (m, 4H), 3.60-3.74 (overlapped m, 1H), 3.66 (s, 2H), 2.62 (t, J=6.6 Hz, 2H), 2.46-2.55 (overlapped m, 4H), 2.39-2.46 (overlapped m, 2H), 1.12-1.22 (m, 2H), 1.00-1.12 (m, 2H). MS1 (ESI, m/z): 538.29 [M+H$^+$]; t$_R$=0.56 min.

Example 13 trans-6-Fluoro-1-methyl-4-oxo-7-(4-{[(3-oxo-3,4-dihydro-2H-pyrido[3,2-b][1,4]thiazin-6-ylmethyl)-amino]-methyl}-cyclohexylamino)-1,4-dihydro-[1,8] naphthyridine-3-carboxylic acid Starting from the compound of Preparation L (60 mg) and 3,4-dihydro-3-oxo-2H-pyrido[3,2-b]-1,4-thiazine-6-carboxaldehyde (31 mg; CAS 443956-16-9; prepared according to WO 2002056882) and proceeding in analogy to example 1, the title compound was obtained, after purification by prep-HPLC, as a white solid (32 mg; 41% yield).

$^1$H NMR (DMSO) δ: 10.81 (s, 1H), 8.85 (s, 1H), 8.09-8.17 (m, 1H), 7.91 (d, J=10.7 Hz, 1H), 7.71 (d, J=7.8 Hz, 1H), 7.07 (d, J=7.8 Hz, 1H), 3.86-4.06 (overlapped m, 1H), 3.90 (s, 3H), 3.66 (s, 2H), 3.50 (s, 2H), 2.37 (d, J=6.4 Hz, 2H), 1.92-2.04 (m, 2H), 1.80-1.92 (m, 2H), 1.31-1.50 (m, 3H), 0.93-1.14 (m, 2H).

MS1 (ESI, m/z): 527.15 [M+H$^+$]; t$_R$=0.63 min.

Example 14 trans-6-Fluoro-1-methyl-4-oxo-7-(4-{[(3-oxo-3,4-dihydro-2H-pyrido[3,2-b][1,4]oxazin-6-ylmethyl)-amino]-methyl}-cyclohexylamino)-1,4-dihydro-[1,8] naphthyridine-3-carboxylic acid Starting from the compound of preparation L (70 mg) and 3-oxo-3,4-dihydro-2H-pyrido[3,2-b][1,4]oxazine-6-carboxaldehyde (40 mg; CAS 443956-11-4; commercial) and proceeding in analogy to example 1, the title compound was obtained, after purification by prep-HPLC, as a white solid (19 mg; 19% yield).

$^1$H NMR (DMSO) δ: 8.85 (s, 1H), 8.16 (s, 1H), 8.13 (d, J=7.6 Hz, 1H), 7.91 (d, J=10.7 Hz, 1H), 7.30 (d, J=8.0 Hz, 1H), 7.01 (d, J=8.0 Hz, 1H), 4.60 (s, 2H), 3.86-4.08 (overlapped m, 1H), 3.90 (s, 3H), 3.70 (s, 2H), 2.36-2.47 (overlapped m, 2H), 1.92-2.05 (m, 2H), 1.81-1.92 (m, 2H), 1.32-1.51 (m, 3H), 0.93-1.14 (m, 2H).

MS1 (ESI, m/z): 511.06 [M+H$^+$]; t$_R$=0.61 min.

Example 15 trans-1-Ethyl-6-fluoro-4-oxo-7-(4-{[(3-oxo-3,4-dihydro-2H-pyrido[3,2-b][1,4]thiazin-6-ylmethyl)-amino]-methyl}-cyclohexylamino)-1,4-dihydro-[1,8] naphthyridine-3-carboxylic acid Starting from the compound of preparation M (73 mg) and 3,4-dihydro-3-oxo-2H-pyrido[3,2-b]-1,4-thiazine-6-carboxaldehyde (43 mg; CAS 443956-16-9; prepared according to WO 2002056882) and proceeding in analogy to example 1, using NaBH$_4$ instead of NaHB(OAc)$_3$, the title compound was obtained, after purification by prep-HPLC, as a white solid (52 mg; 48% yield). $^1$H NMR (DMSO) δ: 10.81 (s, 1H), 8.87 (s, 1H), 8.14 (d, J=7.4 Hz, 1H), 7.90 (d, J=10.7 Hz, 1H), 7.71 (d, J=7.9 Hz, 1H), 7.06 (d, J=7.9 Hz, 1H), 4.44 (q, J=6.4 Hz, 2H), 3.81-4.02 (m, 1H), 3.66 (s, 2H), 3.50 (s, 2H), 2.37 (d, J=6.4 Hz, 2H), 1.92-2.04 (m, 2H), 1.81-1.92 (m, 2H), 1.29-1.52 (overlapped m, 3H), 1.36 (t, J=7.0 Hz, 3H), 0.91-1.14 (m, 2H).

MS1 (ESI, m/z): 541.05 [M+H$^+$]; t$_R$=0.53 min.

Example 16

6-Fluoro-1-methyl-4-oxo-7-(4-{2-[(3-oxo-3,4-dihydro-2H-pyrido[3,2-b][1,4]oxazin-6-ylmethyl)-amino]-ethyl}-piperidin-1-yl)-1,4-dihydro-[1,8] naphthyridine-3-carboxylic acid Starting from the compound of preparation N (359 mg) and 3-oxo-3,4-dihydro-2H-pyrido[3,2-b][1,4]oxazine-6-carboxaldehyde (183 mg; CAS 443956-11-4; commercial) and proceeding in analogy to example 1, the title compound was obtained, after purification by prep-HPLC, as a white solid (123 mg; 23% yield).

$^1$H NMR (DMSO) δ: 11.17 (s, 1H), 8.94 (s, 1H), 8.03 (d, J=13.7 Hz, 1H), 7.31 (d, J=8.0 Hz, 1H), 7.01 (d, J=8.0 Hz, 1H), 4.61 (s, 2H), 4.50 (d, J=13.0 Hz, 2H), 3.93 (s, 3H), 3.39 (q, J=7.0 Hz, 2H), 3.14 (t, J=12.6 Hz, 2H), 2.52-2.61 (overlapped m, 2H), 1.65-1.88 (m, 3H), 1.40 (q, J=6.6 Hz, 2H), 1.16-1.31 (m, 2H).

MS1 (ESI, m/z): 511.03 [M+H$^+$]; t$_R$=0.62 min.

Example 17

6-Fluoro-1-methyl-4-oxo-7-(4-{2-[(3-oxo-3,4-dihydro-2H-pyrido[3,2-b][1,4]thiazin-6-ylmethyl)-amino]-ethyl}-piperidin-1-yl)-1,4-dihydro-[1,8] naphthyridine-3-carboxylic acid Starting from the compound of preparation N (63 mg) and 3,4-dihydro-3-oxo-2H-pyrido[3,2-b]-1,4-thiazine-6-carboxaldehyde (40 mg; CAS 443956-16-9; prepared according to WO 2002056882) and proceeding in analogy to example 1, the title compound was obtained, after purification by prep-HPLC, as a white solid (33 mg; 35% yield).

$^1$H NMR (DMSO) δ: 10.81 (s, 1H), 8.90 (s, 1H), 8.00 (d, J=13.7 Hz, 1H), 7.70 (d, J=7.9 Hz, 1H), 7.05 (d, J=7.8 Hz, 1H), 4.40-4.54 (m, 2H), 3.90 (s, 3H), 3.66 (s, 2H), 3.50 (s, 2H), 3.11 (t, J=12.9 Hz, 2H), 2.53 (t, J=7.0 Hz, 2H), 1.64-1.84 (m, 3H), 1.32-1.46 (m, 2H), 1.10-1.31 (m, 2H).

MS1 (ESI, m/z): 526.94 [M+H$^+$]; t$_R$=0.64 min.

Pharmacological Properties of the Invention Compounds
In Vitro Assays
Bacterial Growth Minimal Inhibitory Concentrations:
Experimental Methods:

Minimal Inhibitory Concentrations (MICs; mg/l) were determined in cation-adjusted Mueller Hinton Broth by a microdilution method following the description given in "Methods for Dilution Antimicrobial Susceptibility Tests for Bacteria that Grow Aerobically", Approved standard, 7th ed., Clinical and Laboratory Standards Institute (CLSI) Document M7-A7, Wayne, Pa., USA, 2006.

Results:

All Example compounds were tested against several Gram positive and especially Gram negative bacteria. Typical antibacterial test results are given in Table 1 hereafter (MICs in mg/L). *Staphylococcus aureus* A798, *Klebsiella pneumoniae* A651 and *Acinetobacter baumanii* T6474 are multiply-resistant strains (in particular quinolone-resistant), while *Moraxella catarrhalis* A894 and *E. coli* ATCC 25922 are quinolone-sensitive strains.

TABLE 1

| Example No. | MIC for S. aureus A798 | MIC for E. coli ATCC 25922 | MIC for M. catarrhalis A894 | MIC for K. pneumoniae A651 | MIC for A. baumanii T6474 |
|---|---|---|---|---|---|
| 1 | 1 | 0.25 | 0.125 | 0.5 | 0.125 |
| 2 | 4 | 0.5 | 0.25 | 1 | 0.5 |
| 3 | 2 | 0.25 | 0.5 | 1 | 4 |
| 4 | >8 | 1 | 0.25 | 2 | 2 |
| 5 | 8 | 0.5 | 0.125 | 2 | 1 |
| 6 | >8 | 2 | 0.5 | 2 | 0.5 |
| 7 | >8 | 0.5 | 0.031 | 4 | 2 |
| 8 | >8 | 0.5 | 0.25 | 8 | >8 |
| 9 | >8 | 1 | 1 | 2 | 8 |
| 10 | 4 | 0.5 | 0.063 | 1 | 0.25 |
| 11 | 8 | 2 | 1 | 8 | >8 |
| 12 | >8 | 2 | 1 | 8 | 8 |
| 13 | 1 | 0.063 | 0.031 | 0.25 | 0.125 |
| 14 | 8 | 0.125 | 0.063 | 1 | 1 |
| 15 | 1 | 0.125 | 0.031 | 0.5 | 0.063 |
| 16 | 2 | 0.25 | 0.125 | 1 | 0.5 |
| 17 | 0.5 | 0.125 | 0.031 | 0.5 | 0.125 |
| Cipro | >8 | <0.016 | <0.016 | >8 | >8 |

The invention claimed is:

1. A compound of formula I

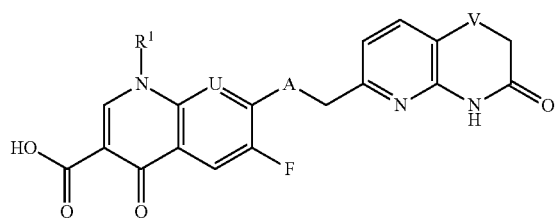

I wherein
$R^1$ represents $(C_1-C_3)$alkyl, or $(C_3-C_5)$cycloalkyl;
U represents CH or N;
V represents O or S; and
A represents a linker of 1-, 2-, or 3-membered saturated straight chain group which is attached to, or interrupted by a 6-membered cyclic group selected from cyclohexan-1,4-diyl, piperidin-1,4-diyl, or piperazin-1,4-diyl; wherein said linker group has a total of two or three nitrogen atoms, wherein said nitrogen atoms are separated from each other by at least two carbon atoms;
or a pharmaceutically acceptable salt thereof.

2. The compound of formula I according to claim 1, wherein
$R^1$ represents methyl or ethyl; or $R^1$ represents cyclopropyl;
U represents CH or N;
V represents O or S;
and
A represents a group selected from:

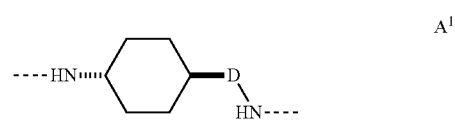

A$^1$

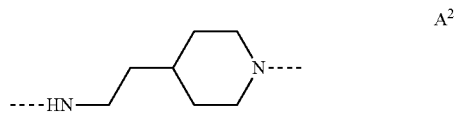

A$^2$

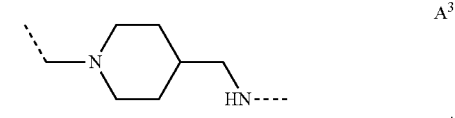

A$^3$

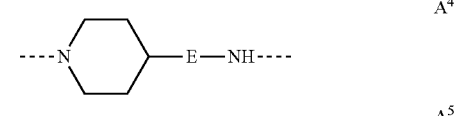

A$^4$

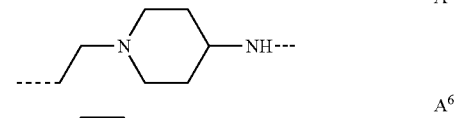

A$^5$

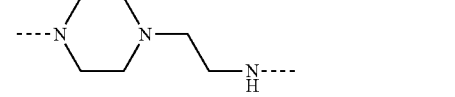

A$^6$ wherein
D represents a bond or $CH_2$; and
E represents a bond, $CH_2$ or $CH_2CH_2$;
or a pharmaceutically acceptable salt thereof.

3. The compound of formula I according to claim 2, wherein $R^1$ represents methyl; or a pharmaceutically acceptable salt thereof.

4. The compound of formula I according to claim 2, wherein $R^1$ represents cyclopropyl; or a pharmaceutically acceptable salt thereof.

5. The compound of formula I according to claim 1, wherein V represents S; or a pharmaceutically acceptable salt thereof.

6. The compound of formula I according to claim 1, wherein U represents N; or a pharmaceutically acceptable salt thereof.

7. The compound of formula I according to claim 1, wherein A represents a group selected from:

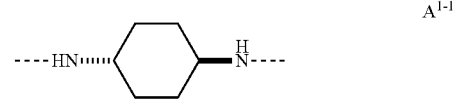

A$^{1\text{-}1}$

-continued

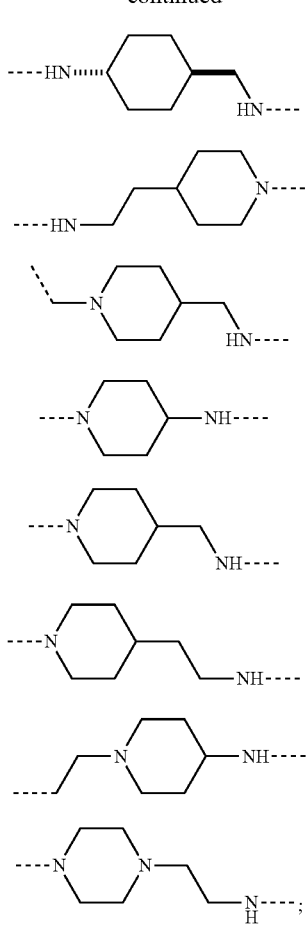

or a pharmaceutically acceptable salt thereof.

8. The compound of formula I according to claim 1, wherein A represents a group selected from:

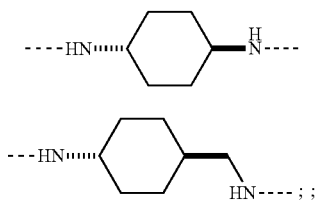

or a pharmaceutically acceptable salt thereof.

9. The compound of formula I according to claim 1, wherein the compound is:

1-Cyclopropyl-6-fluoro-4-oxo-7-(4-{[(3-oxo-3,4-dihydro-2H-pyrido[3,2-b][1,4]thiazin-6-ylmethyl)-amino]-methyl}-cyclohexylamino)-1,4-dihydro-[1,8]naphthyridine-3-carboxylic acid;

1-Cyclopropyl-6-fluoro-4-oxo-7-{4-[(3-oxo-3,4-dihydro-2H-pyrido[3,2-b][1,4]thiazin-6-ylmethyl)-amino]-cyclohexylamino}-1,4-dihydro-[1,8]naphthyridine-3-carboxylic acid;

1-Cyclopropyl-6-fluoro-4-oxo-7-(2-{4-[(3-oxo-3,4-dihydro-2H-pyrido [3,2-b][1,4]thiazin-6-ylmethyl)-amino]-piperidin-1-yl}-ethyl)-1,4-dihydro-[1,8]naphthyridine-3-carboxylic acid;

1-Cyclopropyl-6-fluoro-4-oxo-7-(4-{2-[(3-oxo-3,4-dihydro-2H-pyrido[3,2-b][1,4]thiazin-6-ylmethyl)-amino]-ethyl}-piperazin-1-yl)-1,4-dihydro-[1,8]naphthyridine-3-carboxylic acid;

1-Cyclopropyl-6-fluoro-4-oxo-7-(4-{2-[(3-oxo-3,4-dihydro-2H-pyrido [3,2-b][1,4]thiazin-6-ylmethyl)-amino]-ethyl}-piperidin-1-yl)-1,4-dihydro-[1,8]naphthyridine-3-carboxylic acid;

1-Cyclopropyl-6-fluoro-4-oxo-7-{2-[1-(3-oxo-3,4-dihydro-2H-pyrido[3,2-b][1,4]thiazin-6-ylmethyl)-piperidin-4-yl]-ethylamino}-1,4-dihydro-[1,8]naphthyridine-3-carboxylic acid;

1-Cyclopropyl-6-fluoro-4-oxo-7-(4-{[(3-oxo-3,4-dihydro-2H-pyrido[3,2-b][1,4]thiazin-6-ylmethyl)-amino]-methyl}-piperidin-1-yl)-1,4-dihydro-[1,8] naphthyridine-3-carboxylic acid;

1-Cyclopropyl-6-fluoro-4-oxo-7-(4-{[(3-oxo-3,4-dihydro-2H-pyrido[3,2-b][1,4]oxazin-6-ylmethyl)-amino]-methyl}-cyclohexylamino)-1,4-dihydro-[1,8] naphthyridine-3-carboxylic acid;

1-Cyclopropyl-6-fluoro-4-oxo-7-(4-{[(3-oxo-3,4-dihydro-2H-pyrido[3,2-b][1,4]thiazin-6-ylmethyl)-amino]-methyl}-piperidin-1-ylmethyl)-1,4-dihydro-[1,8]naphthyridine-3-carboxylic acid;

1-Cyclopropyl-6-fluoro-4-oxo-7-{4-{[(3-oxo-3,4-dihydro-2H-pyrido [3,2-b][1,4]thiazin-6-ylmethyl)-amino]-piperidin-1-yl}-1,4-dihydro-[1, 8]naphthyridine-3-carboxylic acid; or 1-Cyclopropyl-6-fluoro-4-oxo-7-(4-{2-[(3-oxo-3,4-dihydro-2H-pyrido [3,2-b][1,4]thiazin-6-ylmethyl)-amino]-ethyl}-piperazin-1-yl)-1,4-dihydro-quinoline-3-carboxylic acid;

or a pharmaceutically acceptable salt thereof.

10. The compound of formula I according to claim 1, wherein the compound is:

1-Cyclopropyl-6-fluoro-4-oxo-7-(4-{2-[(3-oxo-3,4-dihydro-2H-pyrido[3,2-b][1,4]oxazin-6-ylmethyl)-amino]-ethyl}-piperazin-1-yl)-1,4-dihydro-[ 1,8]naphthyridine-3-carboxylic acid;

trans-6-Fluoro-1-methyl-4-oxo-7-(4-{[(3-oxo-3,4-dihydro-2H-pyrido [3,2-b][1,4]thiazin-6-ylmethyl)-amino]-methyl}-cyclohexylamino)-1,4-dihydro-[1,8] naphthyridine-3-carboxylic acid;

trans-6-Fluoro-1-methyl-4-oxo-7-(4-{[(3-oxo-3,4-dihydro-2H-pyrido [3,2-b][1,4]oxazin-6-ylmethyl)-amino]-methyl}-cyclohexylamino)-1,4-dihydro-[1,8] naphthyridine-3-carboxylic acid;

trans-1-Ethyl-6-fluoro-4-oxo-7-(4-{[(3-oxo-3,4-dihydro-2H-pyrido[3,2-b][1,4]thiazin-6-ylmethyl)-amino]-methyl}-cyclohexylamino)-1,4-dihydro-[1,8]naphthyridine-3-carboxylic acid;

6-Fluoro-1-methyl-4-oxo-7-(4-{2-[(3-oxo-3,4-dihydro-2H-pyrido [3,2-b][1,4]oxazin-6-ylmethyl)-amino]-ethyl}-piperidin-1-yl)-1,4-dihydro-[1, 8]naphthyridine-3-carboxylic acid; or 6-Fluoro-1-methyl-4-oxo-7-(4-{2-[(3-oxo-3,4-dihydro-2H-pyrido [3,2-b][1,4]thiazin-6-ylmethyl)-amino]-ethyl}-piperidin-1-yl)-1,4-dihydro-[1,8]naphthyridine-3-carboxylic acid;

or a pharmaceutically acceptable salt thereof.

11. The compound of formula I according to claim 1, formulated as a medicament, or a pharmaceutically acceptable salt thereof.

12. A pharmaceutical composition comprising, as active principle, the compound of formula I according to claim 1, or a pharmaceutically acceptable salt thereof, and at least one therapeutically inert excipient.

13. A method of treating a bacterial infection comprising administering to a subject in need thereof a compound according to claim 1.

14. The method according to claim 13, wherein said bacterial infection is nosocomial pneumonia, urinary tract infections, systemic infections, skin and soft tissue infections, surgical infections, intraabdominal infections, lung infections, endocarditis, diabetic foot infections, osteomyelitis, or central nervous system infections.

15. The method according to claim 13, wherein said bacterial infection is mediated by fermentative or non-fermentative Gram negative bacteria.

16. The method according to claim 13, wherein said bacterial infection is mediated by *Acinetobacter baumannii, Burkholderia, Citrobacter* spp., *Enterobacter aerogenes, Enterobacter cloacae, Escherichia coli, Klebsiella oxytoca, Klebsiella pneumoniae, Serratia marcescens, Stenotrophomonas maltophilia,* or *Pseudomonas aeruginosa.*

\* \* \* \* \*